US008674121B2

(12) United States Patent
Kretzschmar et al.

(10) Patent No.: US 8,674,121 B2
(45) Date of Patent: Mar. 18, 2014

(54) PROCESS FOR THE PRODUCTION OF BENZOFURANS

(75) Inventors: Gerhard Kretzschmar, Frankfurt am Main (DE); Volker Kraft, Frankfurt am Main (DE); Thomas Olpp, Frankfurt am Main (DE); Kai Rossen, Frankfurt am Main (DE)

(73) Assignee: SANOFI, Paris (FR)

( * ) Notice: Subject to any disclaimer, the term of this patent is extended or adjusted under 35 U.S.C. 154(b) by 179 days.

(21) Appl. No.: 13/321,754

(22) PCT Filed: May 26, 2010

(86) PCT No.: PCT/EP2010/057270
§ 371 (c)(1),
(2), (4) Date: Nov. 21, 2011

(87) PCT Pub. No.: WO2010/136500
PCT Pub. Date: Dec. 2, 2010

(65) Prior Publication Data
US 2012/0065411 A1  Mar. 15, 2012

Related U.S. Application Data

(60) Provisional application No. 61/244,550, filed on Sep. 22, 2009.

(30) Foreign Application Priority Data

May 27, 2009  (EP) ..................................... 09290395

(51) Int. Cl.
*C07D 307/80* (2006.01)
(52) U.S. Cl.
USPC ........................................................ 549/467
(58) Field of Classification Search
USPC ........................................................ 549/467
See application file for complete search history.

(56) References Cited

U.S. PATENT DOCUMENTS

| 3,577,441 | A | 5/1971 | Kaminsky et al. |
| 3,657,350 | A | 4/1972 | Mooradian et al. |
| 5,223,510 | A | 6/1993 | Gubin et al. |
| 2012/0077995 | A1 | 3/2012 | Kretzschmar et al. |

FOREIGN PATENT DOCUMENTS

| EP | 0471609 A1 | 2/1992 |
| FR | 2809397 | 11/2001 |
| FR | 2833259 | 6/2003 |
| WO | WO 01/28974 A2 | 4/2001 |
| WO | WO 01/29019 A1 | 4/2001 |
| WO | WO 02/48078 A1 | 6/2002 |
| WO | WO03/040120 A1 | 5/2003 |
| WO | WO 2006/021304 A1 | 3/2006 |
| WO | WO 2007/140989 A2 | 12/2007 |
| WO | WO2009/044143 A2 | 4/2009 |
| WO | WO 2010/136502 A1 | 12/2010 |

OTHER PUBLICATIONS

International Preliminary Report on Patentability dated Nov. 29, 2011 issued in PCT/EP2010/057270.
Wu, et al., Immobilization of HX: [HmIm]X as Halogenating Agent, Recyclable Catalyst and Medium for Conversion of Alcohols to Alkyl Halides, Chinese Journal of Chemistry, vol. 22, pp. 619-621 (2004).
Boovanahalli, et al., Application of Ionic Liquid Halide Nucleophilicity for the Cleavage of Ethers: A Green Protocol for the Regeneration of Phenols From Ethers, J. Org. Chem., vol. 69, pp. 3340-3344, (2004).
Castellino, et al., Synthesis of Benzofurans from Oxgenated Phenoxyamines, J. Org. Chem., (1984), vol. 49, pp. 4399-4404.
Chauhan, et al., Microwave Assisted Dealkylation of Alkyl Aryl Ethers in Ionic Liquids, Journal of Chemical Research, (2004), pp. 693-694.
Cheng, et al., Facile Cleavage of Ethers in Ionic Liquid, Bull. Chem. Soc. Jpn., vol. 80, No. 10, pp. 2008-2010, (2007).
Delahay, et al., Past and Recent Approaches of Preparing Fe-ZSM-5, Current Topics in Catalysis, (2007), vol. 6, pp. 19-33.
Fieser, et al., Reagents for Organic Synthesis, John Wiley & Sons, p. 703-705 (1967).
Gutowski, et al., Prediction of the Formation and Stabilities of Energetic Salts and Ionic Liquids Based on ab initio Electronic Structure Calculations, J. Phys. Chem. B. (2005), vol. 109, pp. 23196-23208.
Headley, et al., Dynamic Solvation in Imidazolium-Based Ionic Liquids on Short Time Scales, J. Phys. Chem. A, (2006), vol. 110, pp. 9549-9554.
Horton, et al., [65] Reactions With Reactive Alkyl Halides, J. Methods in Enzymology, vol. 11, pp. 556-565, (1967).
Imori, et al., Efficient Demethylation of N,N-Dimethyanilines With Phenyl Chloroformate in Ionic Liquids, Synlett, (2006), No. 16, pp. 2629-2632.
Laszlo, et al., 65. Catalysis of Friedel-Crafts Alkylation by a Montmorillonite doped with Transition-Metal Cations, Helvetica Chimica Acta, vol. 70, (1987), pp. 577-586.
Liu, et al., Cleavage of Methyl Ethers of Flavones by Chloroaluminate Ionic Liquid, Synthetic Communications, (2004), vol. 34, pp. 3209-3218.
Majdik, et al., O-Arilcetoxime I. O-Arilarea Cetoximelor cu Nitroclorbenzeni, Revista De Chimie, vol. 40, No. 6, (1989), pp. 490-493.
Majdik, et al., O-Arilcetoxime II. Prepararea Unor 2-(Aril)-Nitrobenzofurani Din O-(Nitrofenil)-Acetofenonoxime, Revista De Chimie, vol. 40, No. 8, (1989), pp. 689-693.
Nagy, et al., Isomorphous Substitution in Zeolites, Mol. Sieves, (2007), vol. 5, pp. 365-478.
Nakamura, et al., Pyrazole Derivatives as New Potent and Selective 20-Hydroxy-5,8,11,14-Eicosatetraenoic Acid Synthase Inhibitors, Bioorganic & Medicinal Chemistry, vol. 12, (2004), pp. 6209-6219.
Pal, et al., Synthesis of Monohydroxy-Functionalized Triphenylene Discotics: Green Chemistry Approach, Tetrahedron, vol. 63, (2007), pp. 6874-6878.

(Continued)

*Primary Examiner* — Taofiq A Solola
(74) *Attorney, Agent, or Firm* — Scully, Scott, Murphy & Presser, P.C.

(57) ABSTRACT

A process for the production of 2-alkyl-3-aroyl-5-nitrobenzofurans by acylation of 2-(2-hydroxy-5-nitrophenyl)-1-arylethanones and subsequent treatment of the esters with combinations of bases and proton acids or Lewis acids. This process can be used for the production of Dronedarone. Furthermore, novel intermediates for the manufacture of Dronedarone are provided.

21 Claims, No Drawings

(56) References Cited

OTHER PUBLICATIONS

Skeels, et al., Zeolite Chemistry, Substitution of Iron or Titanium for Aluminum in Zeolites via Reaction With The Respective Ammonium Fluoride Salts, ACS Symposium Series, Zeolite Synthesis, (1989), vol. 398, pp. 420-435.

Weissman, et al., Recent Advances in Ether Dealkylation, Tetrahedron, vol. 61, (2005), pp. 7833-7863.

Weitkamp, et al., Isomorphe Substitution in Zeolithen: Katalyse an Boro-, Alumo- und Gallo-Silicaten mit ZSM-5-Struktur, Chem.-Ing.-Tech., vol. 58, (1986), No. 12, pp. 969-971.

Fontana, et al., Syntheses of (R,S)-Naproxen and Its 6-O-Desmethylated Metabolite Labelled With 2H, Journal of Labelled Compounds and Radiopharmaceuticals, (2008), vol. 51, pp. 239-241.

Adams et al., "Quinone Imides. XXXIX. Adducts of Quinone Monoimides and Conversion of Active Methylene Adducts to Benzofurans," Journal of the American Chemical Society (1956), vol. 78, No. 3, pp. 658-663.

Majdik et al., "Cyclization of hydroxybenzyl phenyl ketones in benzofuran derivatives," Revista de Chimie (1985), vol. 36, No. 8, pp. 760-761.

International Search Report dated Sep. 22, 2010 issued in PCT/EP2010/057270.

PROCESS FOR THE PRODUCTION OF BENZOFURANS

CROSS-REFERENCE TO RELATED APPLICATIONS

This application claims the benefit of U.S. Provisional Application No. 61/244,550 filed on Sep. 22, 2009.

A process for the production of 2-alkyl-3-aroyl-5-nitrobenzofurans by acylation of 2-(2-hydroxy-5-nitrophenyl)-1-aryl-ethanones and subsequent treatment of the esters with combinations of bases and proton acids or Lewis acids. This process can be used for the production of Dronedarone. Furthermore, novel intermediates for the manufacture of Dronedarone are provided.

The present invention relates to a chemical process for the manufacture of 2-alkyl-3-aroyl-5-nitro-benzofurans of the formula I and their use as intermediates in the production of drugs. For instance, 2-n-butyl-3-(4-methoxybenzoyl)-5-nitrobenzofuran of the formula I, wherein R1 is n-butyl and R2 is OMe, (=compound of the formula Ia) is a key intermediate for the production of N-(2-n-butyl-3-{4-[3-(dibutylamino)-propoxy]-benzoyl}-benzofuran-5-yl)-methanesulfonamide of the formula II (Dronedarone)

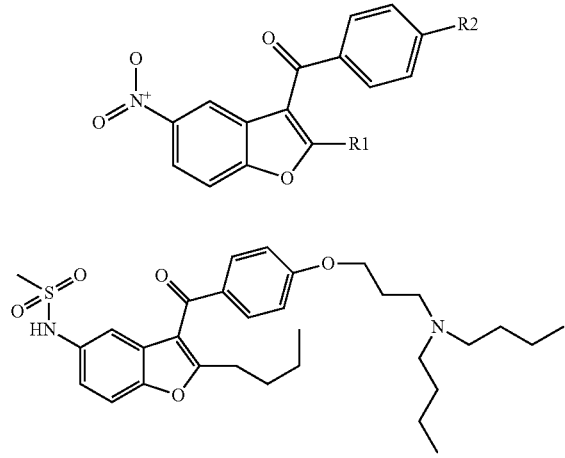

I

II

Dronedarone is a drug for the treatment of arrhythmia (U.S. Pat. No. 5,223,510) and several prior art methods are disclosed for its preparation. These methods involve stepwise procedures via a number of intermediates, of which two examples are 2-n-butyl-5-nitrobenzofuran of the formula III and 2-n-butyl-3-(4-methoxybenzoyl)-5-nitrobenzofuran of the formula Ia.

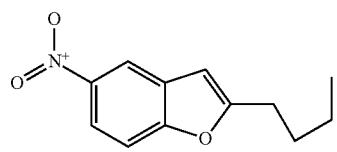

III

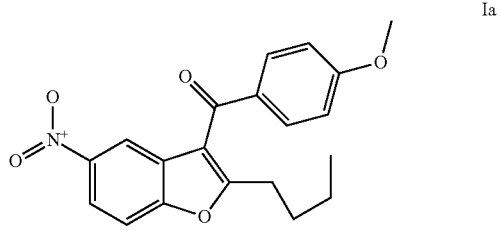

Ia

The intermediate of the formula III is prepared by multistage processes from 4-nitrophenol as described in U.S. Pat. No. 5,223,510 and H. R. Horton and D. E. Koshland, J. Methods in Enzymology, Vol. 11, 556, (1967) or from salicylaldehyde as described in WO0128974 and WO0129019.

The intermediate of the formula Ia is conventionally prepared from the intermediate of the formula III by Friedel Crafts benzoylation with anisoyl chloride and heavy metal Lewis-acids, like tin-tetrachloride or iron(III)chloride as catalysts in halogenated or non-halogenated solvents, as described in WO2007140989 and other references described therein.

It is an object of the present invention to provide a novel process for the preparation of 2-alkyl-3-aroyl-5-nitro-benzofurans of the formula I starting either from commercially available materials or compounds described already in the literature, themselves being prepared easily from commercially available materials, by using simple and environmentally compatible reagents and solvents, to afford high overall yields and good purity of the products.

The above object is achieved in accordance with the present invention—which, in one aspect thereof, provides a process for preparing an intermediate leading to Dronedarone—starting with commercially available compounds such as 4-methoxyacetophenone, 4-benzyloxyacetophenone, 4-chloroacetophenone, 4-bromoacetophenone, 4-fluoroacetophenone, 4-chloronitrophenol and valeric acid chloride (pentanoylchloride).

One aspect of the present invention thus relates to a process for preparing a compound of the formula I

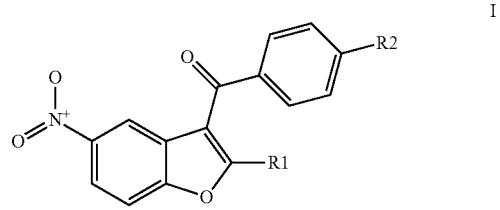

I according to method 1, wherein

R1 is alkyl having 1, 2, 3, 4, 5, 6, 7, 8, 9, 10, 11 or 12 carbon atoms or cycloalkyl having 3, 4, 5, 6 or 7 carbon atoms;

R2 is methoxy, $OCH_2C_6H_5$, F, Cl, Br or $OCH_2CH_2CH_2N(CH_2CH_2CH_2CH_3)_2$;

and salts thereof;

which comprises, as shown in scheme 1,

Scheme 1

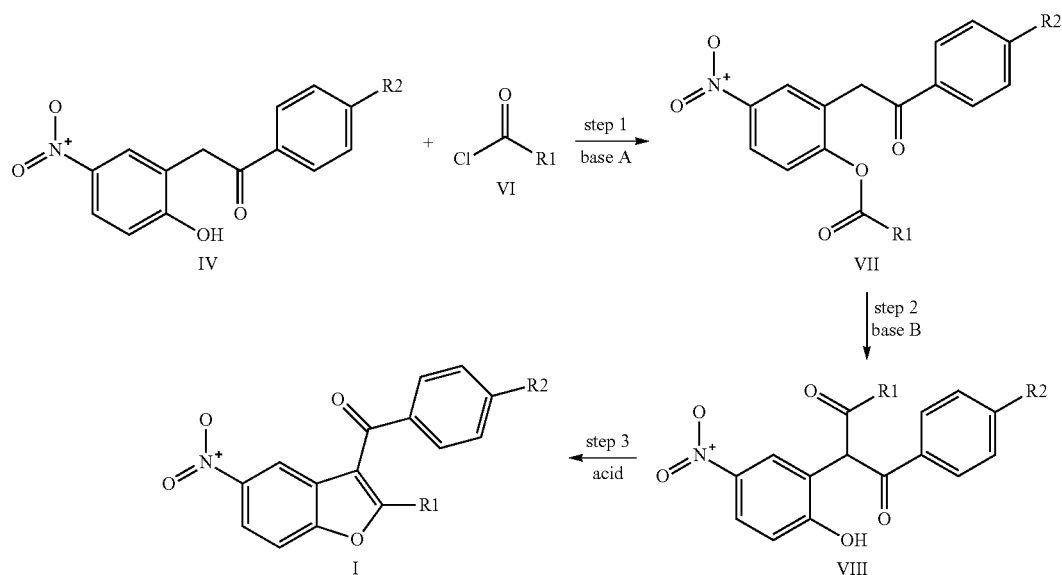

a) acylation of the 2-(2-hydroxy-5-nitrophenyl)-1-aryl-ethanone of the formula IV by the acid chloride of formula VI in the presence of a base A providing the new ester of the formula VII (step 1);
b) treatment of the ester of the formula VII with a base B providing the 1,3-diketone of the formula VIII (step 2);
c) heating of the 1,3-diketone of formula VIII in an acid providing the compound of the formula I (step 3);
wherein, in the compounds of the formulae IV, VI, VII and VIII R1 and R2 are each as defined in formula I.

In one embodiment the compound of formula I is prepared according to method 1, wherein R1 is alkyl having 1, 2, 3, 4, 5, 6, 7, 8, 9, 10, 11 or 12 carbon atoms, for example alkyl having 1, 2, 3, 4, 5 or 6 carbon atoms, preferably n-butyl, and R2 is methoxy, F, Cl, Br or $OCH_2CH_2CH_2N(CH_2CH_2CH_2CH_3)_2$ (dibutylaminopropoxy), preferably methoxy, Cl or dibutylaminopropoxy.

In a preferred embodiment the compound of formula I is prepared according to method 1, wherein R1 is n-butyl and R2 is methoxy.

In another preferred embodiment the compound of formula I is prepared according to method 1, wherein R1 is n-butyl and R2 is Cl.

In another preferred embodiment the compound of formula I is prepared according to method 1, wherein R1 is n-butyl and R2 is dibutylaminopropoxy.

The present invention also relates to a process for preparing a compound of the formula I

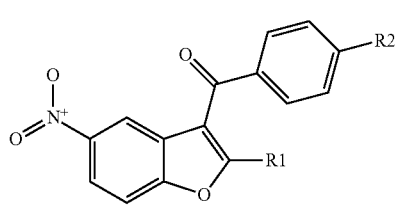

according to method 2, wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, $OCH_2C_6H_5$, F, Cl, Br or $OCH_2CH_2CH_2N(CH_2CH_2CH_2CH_3)_2$;
and salts thereof;
which comprises, as shown in scheme 2, Scheme 2

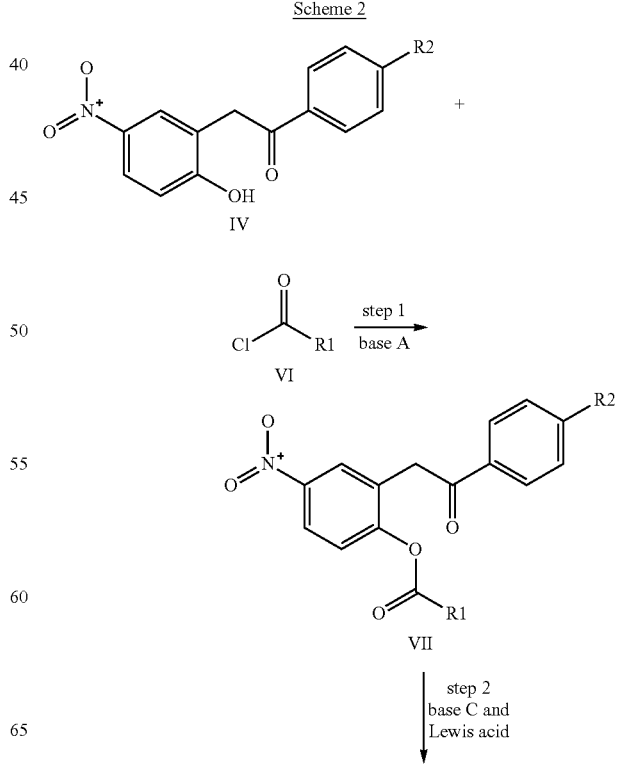

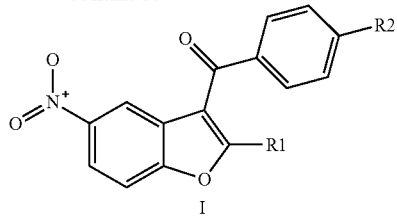

a) acylation of the 2-(2-hydroxy-5-nitrophenyl)-1-aryl-ethanone of the formula IV by the acid chloride of formula VI in the presence of a base A providing the new ester of the formula VII (step 1);
b) transformation of the ester of the formula VII into the compound of the formula I by using a base C in combination with a Lewis acid (step 2);
wherein, in the compounds of the formulae IV, VI and VII R1 and R2 are each as defined in formula I.

In one embodiment the compound of formula I is prepared according to method 2, wherein R1 is alkyl having 1, 2, 3, 4, 5, 6, 7, 8, 9, 10, 11 or 12 carbon atoms, for example alkyl having 1, 2, 3, 4, 5 or 6 carbon atoms, preferably n-butyl, and R2 is methoxy, F, Cl, Br or $OCH_2CH_2CH_2N(CH_2CH_2CH_2CH_3)_2$ (dibutylaminopropoxy), preferably methoxy, Cl or dibutylaminopropoxy.

In a preferred embodiment the compound of formula I is prepared according to method 2, wherein R1 is n-butyl and R2 is methoxy.

In another preferred embodiment the compound of formula I is prepared according to method 2, wherein R1 is n-butyl and R2 is Cl.

In another preferred embodiment the compound of formula I is prepared according to method 2, wherein R1 is n-butyl and R2 is dibutylaminopropoxy.

In addition, the 1,3-diketones of formula VIII which are produced in step 2 of method 1 are likewise suited to perform the reaction step 2 of method 2 under the same reaction conditions. Therefore, one further embodiment of the invention is to provide a combination of both methods by first executing steps 1 and 2 according to method 1 to deliver the 1,3-diketones of formula VIII, in isolated or non-isolated form, which then are subjected to the reaction conditions employed in step 2 of method 2 to produce the compounds of formula I.

Therefore, the present invention also relates to a process for preparing a compound of the formula I

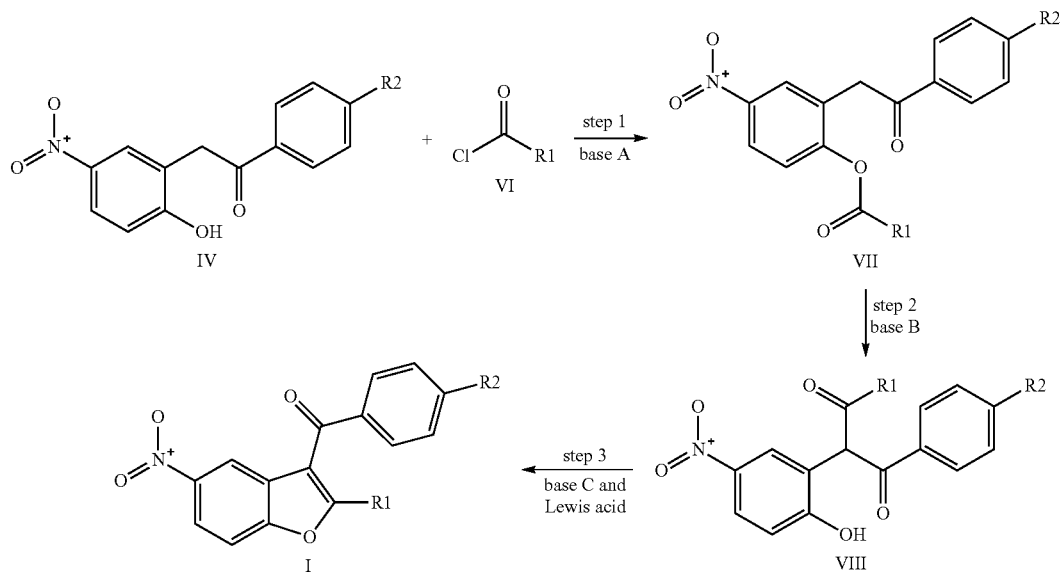

according to method 3, wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, $OCH_2C_6H_5$, F, Cl, Br or $OCH_2CH_2CH_2N(CH_2CH_2CH_2CH_3)_2$;
and salts thereof;
which comprises, as shown in scheme 3, Scheme 3 a) acylation of the 2-(2-hydroxy-5-nitrophenyl)-1-aryl-ethanone of the formula IV by the acid chloride of formula VI in the presence of a base A providing the new ester of the formula VII (step 1);
b) treatment of the ester of the formula VII with a base B providing the 1,3-diketone of the formula VIII (step 2);
c) transformation of the 1,3-diketone of the formula VIII into the compound of the formula I by using a base C in combination with a Lewis acid (step 3);
wherein, in the compounds of the formulae IV, VI, VII and VIII R1 and R2 are each as defined in formula I.

In one embodiment the compound of formula I is prepared according to method 3, wherein R1 is alkyl having 1, 2, 3, 4, 5, 6, 7, 8, 9, 10, 11 or 12 carbon atoms, for example alkyl having 1, 2, 3, 4, 5 or 6 carbon atoms, preferably n-butyl, and R2 is methoxy, F, Cl, Br or OCH$_2$CH$_2$CH$_2$N(CH$_2$CH$_2$CH$_2$CH$_3$)$_2$ (dibutylaminopropoxy), preferably methoxy, Cl or dibutylaminopropoxy.

In a preferred embodiment the compound of formula I is prepared according to method 3, wherein R1 is n-butyl and R2 is methoxy.

In another preferred embodiment the compound of formula I is prepared according to method 3, wherein R1 is n-butyl and R2 is Cl.

In another preferred embodiment the compound of formula I is prepared according to method 3, wherein R1 is n-butyl and R2 is dibutylaminopropoxy.

The preparation of the starting material of the formula IV is either explicitly described in the literature (for example U.S. Pat. Nos. 3,657,350, 3,577,441, C. Majdik et al., Revista de Chimie 40 (6), 490-3 (1989) and 40 (8), 689-93 (1989) (Bukarest)) or can be performed according to the procedures described therein from the respective 4-substituted acetophenone derivatives 4-methoxyacetophenone, 4-benzyloxyacetophenone, 4-chloroacetophenone, 4-bromoacetophenone, 4-fluoroacetophenone or 4-[3-(dibutylamino)-propoxy]-acetophenone.

The starting compounds of the formula VI are commercially available or can be prepared according to or in a similar manner to the processes described in the literature and are familiar to those skilled in the art.

The following describes each of the distinct process steps of the invention in more detail:

Step 1 according to method 1, method 2 and method 3 describes the esterification of the compounds of the formula IV with an aliphatic acid chloride of the formula VI which requires base A to neutralise the acid which is liberated in the esterification step. At least one equivalent of such base is needed for this purpose, its nature being not critical, since any base neutralising HCl can be taken, including a metal carbonate, a metal hydroxide, a metal alcoholate, a tertiary amine, or the like. Examples of base A are triethylamine, diisopropylethylamine, tri-n-butylamine, pyridine, 4-dimethylaminopyridine, NaOH, KOH, Na$_2$CO$_3$ and K$_2$CO$_3$. In one embodiment base A is preferably Na$_2$CO$_3$ and K$_2$CO$_3$.

In a special embodiment step 1 comprises at first as shown in scheme 4 the neutralisation of the acidic OH-moiety in the compound of the formula IV with one of the above-mentioned hydroxides or carbonates (base A*) in order to obtain the crystalline sodium or potassium salts of the formula V, Scheme 4

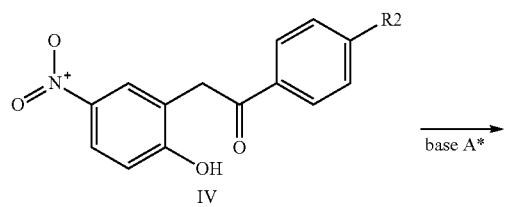

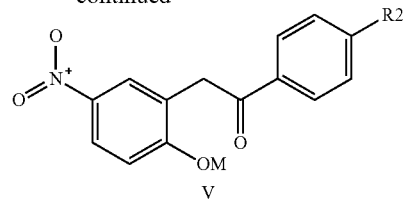

wherein
R2 is methoxy, OCH$_2$C$_6$H$_5$, F, Cl, Br or OCH$_2$CH$_2$CH$_2$N(CH$_2$CH$_2$CH$_2$CH$_3$)$_2$;
M is Na or K;
Base A* is a metal carbonate or a metal hydroxide, for example NaOH, KOH, Na$_2$CO$_3$ and K$_2$CO$_3$, preferably Na$_2$CO$_3$ and K$_2$CO$_3$.

The sodium or potassium salts of formula V can be used as a stable storage form.

For instance, the phenols of the formula IV can be dispersed in a minimum amount of water and neutralized with approximately one base equivalent of above base A* at 0° C. to 100° C., preferably at 0° C. to 50° C. The resulting sodium or potassium salts of the formula V, respectively, can be isolated, for example by precipitation, and can be filtered and dried afterwards. Alternatively, the salts of the formula V can be prepared in organic solvents, for example acetone, methylethylketon or acetonitril, preferably acetone, by neutralisation with about one equivalent of said bases in water at 0° C. to 100° C., preferably at 0° C. to 50° C., for example at 40-50° C., and the products can be isolated, for example by evaporation of the solvents.

In one embodiment of the invention the phenol esters of the formula VII can be obtained by mixing the phenols of the formula IV with one equivalent amount or a slight excess, for example 1.0 to 1.5 equivalents, of the acid chloride of the formula VI in an inert organic solvent, for example N,N-dimethylformamide, tetrahydrofuran, acetone, dichloromethane, methyl-isobutyl ketone, acetonitrile, 2-methyl-tetrahydrofuran, 1,4-dioxan, toluene, benzene, ethyl acetate or isopropyl acetate, with base A, at −20° C. to +50° C., preferably at 0° C.-20° C. The products of the formula VII can be isolated in a way known by a person skilled in the art. For example by washing away excess acid and acid chloride with diluted aqueous bases, for example NaHCO$_3$ or KHCO$_3$, washing away excess base with diluted aqueous acids, for example HCl, citric acid or NaH$_2$PO$_4$, preferably HCl, drying the organic phase for example with MgSO$_4$ or Na$_2$SO$_4$, and evaporation of solvents.

Alternatively, the respective sodium or potassium salt of the formula V can be combined with about one equivalent of the acid chloride of the formula VI in a volatile inert organic solvent for example tetrahydrofuran, acetone, dichloromethane, methyl-ethyl ketone, methyl-isobutyl ketone, acetonitrile, 2-methyl-tetrahydrofuran, 1,4-dioxan, toluene, preferably acetone, at −20° C. to +50° C., preferably at −10° C. to 20° C. The reaction solution can be directly subjected to the subsequent step 2 or the product can be isolated by filtration from the precipitated sodium or potassium chloride and evaporation of solvents.

By any procedure described here, the esters of the formula VII are obtained in practically quantitative yield and good purity for the following reaction step 2.

Step 2 according to method 1 and method 3 comprises the treatment of the esters of the formula VII with a base (base B) in a solvent or without solvent to give the 1,3-diketones of formula VIII. For that purpose, the esters of the formula VII are treated in pure form, dissolved or suspended in an inert organic solvent, preferably in a minimum amount of an inert organic solvent, for instance in N,N-dimethylformamide, N-methylpyrrolidone, acetone, dichloromethane, methyl-isobutyl ketone, acetonitrile, toluene, tetrahydrofuran (THF), 2-methyl-tetrahydrofuran or 1,4-dioxan, preferably tetrahydrofuran, dichloromethane, methyl-isobutyl ketone, toluene or 2-methyl-tetrahydrofuran, with one equivalent or a slight excess, for example 1.0 to 2.0 equivalents, of base B. Examples for base B performing the desired process include the following bases: potassium-carbonate, sodium-carbonate, cesium-carbonate, sodium-hydride, potassium-hydride, lithium-bis(trimethylsilyl)amide, potassium-bis(trimethylsilyl)amide, sodium- or potassium-tert-butoxide, sodium- or potassium-tert.-pentoxide, lithium-diisopropylamide, tetraalkylammonium-hydroxide or -acetate wherein alkyl in each alkyl residue is independently of each other methyl, ethyl, propyl, butyl or decyl and wherein one or more alkyl residues can be replaced by benzyl, a 1,3-dialkyl-imidazolium alkanoate, wherein each alkyl residue is independently of each other methyl, ethyl, propyl or butyl and wherein alkanoate is acetate, propionate butyrate, pivaloate or valerate, 1,1,3,3,-tetramethyl-guanidine (TMG), 2-tert.-butyl-1,1, 3,3,-tetramethyl-guanidine (t-Bu-TMG), 1,1,2,3,3-pentamethyl-guanidine, 1,5-diazabicyclo[4.3.0]non-5-ene (DBN), 1,8-diazabicyclo[5.4.0]undec-7-ene (DBU), 7-methyl-1,5,7-triazabicyclo[4.4.0]dec-5-ene (MTBD), 1,5,7-triazabicyclo [4.4.0]dec-5-ene (TBD), or a phosphazene base like 2-tert.-butylimino-2-diethylamino-1,3-dimethyl-perhydro-1,3,2-diazaphosphorine (BEMP) and related non-nucleophilic phospazene bases. The preferred base B for step 2 is selected from the group of potassium carbonate, lithium-bis(trimethylsilyl)-amide, tetramethylammonium-acetate, 1,1,3,3,-tetramethyl-guanidine (TMG), 1,1,2,3,3-pentamethylguanidine, 2-tert.-butyl-1,1,3,3,-tetramethyl-guanidine (t-Bu-TMG), 1,5-diazabicyclo[4.3.0]non-5-ene (DBN) and 1,8-diazabicyclo[5.4.0]undec-7-ene (DBU), for example lithium-bis(trimethylsilyl)amide, tetramethylammonium-acetate, 1,1,3,3,-tetramethyl-guanidine (TMG), 2-tert.-butyl-1, 1,3,3,-tetramethyl-guanidine (t-Bu-TMG) and 1,8-diazabicyclo[5.4.0]undec-7-ene (DBU). The temperature for the reaction in process step 1 can be from −50° C. to 50° C., preferably from −10° C. to 40° C.

The reaction times of step 2 are variable and, as a person skilled knows, depend on the base, the solvent and the temperature selected for this process. A typical reaction time when using TMG. DBU or t-Bu-TMG as a base ranges from several hours to one minute when the reaction temperature ranges from −40° C. to +30° C., for example 5° C. to 25° C. In addition, it is recommended to control the reaction turn-over by monitoring the reaction, for example using reversed phase high pressure liquid chromatography techniques (RP-HPLC) before submitting the mixture to the next reaction step. High turnover rates in this reaction step are achieved when using dry solvents and bases. Otherwise the remaining water in the solvents or bases can lead to hydrolysis of the ester resulting in the formation of the respective precursor compounds of the formula IV. The 1,3-diketones of the formula VIII can be isolated, for example by means of RP-HPLC, and their structure can be verified by spectroscopic methods, such as nuclear magnetic resonance spectroscopy. If isolated in this way or prepared by any other means, compounds of the formula VIII may be subjected to the next step 3 according to method 1 or 3.

The 1,3-diketones of the formula VIII can either be isolated and then supplied to the next step 3 (method 1 or 3) or can be prepared in situ without being isolated and directly used in the next step 3 (method 1 or 3). Preferably the intermediates VIII are not isolated but subjected directly to the next step 3 according to method 1 or 3.

Step 3 according to method 1 comprises the treatment of the 1,3-diketones of the formula VIII with an acid.

One embodiment of the invention, but not limited to it, takes the reaction mixture obtained from step 2 and transfers it into a pre-heated reaction flask containing an acid eligible to perform the conversion into the desired compounds of the formula I. Therefore, the compound of the formula VIII is already dissolved in the inert organic solvent used in step 2 or can be dissolved in of an inert organic solvent, for example dichloromethane, methyl-isobutyl ketone, toluene or 2-methyl-tetrahydrofuran, Examples of the acids which are suitable to perform this conversion include acetic acid, 2-chloroacetic acid, methoxy-acetic acid, propionic acid, butyric acid, valeric acid or pivalic acid, preferably acetic acid or methoxy-acetic acid. The acid is used in excess, typically 2 to 10 equivalents, for example 3.0 to 9.0 equivalents, of one of these acids, or of a mixture of at least two of these acids is used. The reaction temperature ranges from 20° C. to 180° C., preferably from 30° C. to 110° C., in dependence of the solvents and acids used in the reaction step. The reaction time ranges from 20 minutes to 48 hours, in dependence of the reaction temperature and of the acids and solvents used. Typically, the reaction time ranges from 1 hour to 21 hours within reaction temperatures from 50° C. to 110° C., for example from 75-85° C., when using acetic acid or methoxy-acetic acid. The reaction turnover can be monitored, for example by RP-HPLC, until all the 1,3-diketone of the formula VIII has been consumed, before isolating the products of the formula I.

Step 2 according to method 2 comprises the treatment of the esters VII with a base C in the presence of a Lewis acid. Examples for bases C performing the desired reaction include triethylamine, tri-n-butylamine, tri-n-propylamine, N-methylimidazol, diisopropylethylamine or sparteine, preferably triethylamine or diisopropylethylamine. Examples for Lewis acids performing the desired reaction include titanium-tetrachloride ($TiCl_4$), aluminium-chloride ($AlCl_3$), zinc-chloride ($ZnCl_2$), zinc-bromide ($ZnBr_2$), iron-chlorides ($FeCl_2$ and $FeCl_3$), iron-acetylacetonates ($Fe[acac]_2$ and $Fe[acac]_3$), iron-acetates ($Fe[OAc]_2$) and $Fe[OAc]_3$), manganese-dichloride ($MnCl_2$), manganese-dibromide ($MnBr_2$), manganese-acetates ($Mn[OAc]_3$ and $Mn[OAc]_3$), manganese-acetylacetonates ($Mn[acac]_3$ and $Mn[acac]_2$), zirconium-tetrachloride ($ZrCl_4$), scandium triflate ($Sc[OSO_2CF_3]_3$), scandium-trichloride ($ScCl_3$), tin-tetrachloride ($SnCl_4$), bismuth-triflate ($Bi[OSO_2CF_3]_3$), indium-triflate ($In[OSO_2CF_3]_3$), and cerium-trichloride (CeCl3), preferably titanium-tetrachloride ($TiCl_4$), iron-chlorides ($FeCl_2$ and $FeCl_3$), manganese-dichloride ($MnCl_2$), aluminium-chloride ($AlCl_3$), zinc-chloride ($ZnCl_2$), zirconium-tetrachloride ($ZrCl_4$) and tin-tetrachloride ($SnCl_4$). More preferred Lewis acids are $FeCl_3$, $TiCl_4$, $MnCl_2$, $AlCl_3$ and $ZnCl_2$.

For convenience the reaction is usually performed in an inert solvent, but in some cases it is also possible to run the reaction without a solvent. Examples for inert solvents in which the reaction can be performed include dichloromethane, 1,2-dichloroethane, chlorobenzene, toluene, xylene, acetonitrile, 1,2-dichlorobenzene, nitrobenzene and trifluoromethylbenzene, preferably dichlormethane, acetonitrile and toluene.

The stoichiometry can vary widely and will have an influence on the reaction rate, the product yield and purity. For example about 0.001 to 1.5 molar equivalents of the selected Lewis acid and 0.9 to 3.0 molar equivalents of the selected base can be used, preferably 0.01 to 1.2 equivalents of the selected Lewis acid and 1.0 to 2.0 molar equivalents of the selected base. As a person skilled in the art knows the reaction rate and product yield and purity is a function of the bases and Lewis acids employed as well as the reaction temperature and the solvent used. The reaction temperature can vary widely from −80° C. to 140° C. When performing the reaction with the TiCl₄ and triethylamine, the temperature ranges from −20° C. up to +90° C., preferably from 30° C. to 70° C., more preferably from 35° C. to 40° C., in dependence of the solvent used. When performing the reaction with the FeCl₃ and tri-n-butylamine, the temperature ranges from 60° C. up to +140° C., preferably from 80° C. to 120° C., more preferably from 100° C. to 110° C., in dependence of the solvent used.

Step 3 according to method 3 comprises the treatment of the 1,3-diketones VIII with a base C in the presence of a Lewis acid under the same reaction conditions as described for step 2 according to method 2.

The compound of the formula I obtained by method 1, 2 or 3 can be isolated with methods known to those skilled in the art. These procedures can include an aqueous work-up of the reaction mixture or a chromatography of the reaction mixture. Chromatographic techniques are useful, especially if hydrolysis has led to the formation of some compound of the formula IV. An example of an easy work-up procedure involves removing excessive acid, for example by distillation of the acid from the reaction mixture and addition of an excess of aqueous sodium hydroxide or potassium hydroxide. In certain instances, this procedure allows the recovery of some precursor compound of the formula IV, if being formed by hydrolysis during the reaction, in form of the crystalline sodium or potassium salt V in good yield and purity. The desired product of the formula I can be extracted from the reaction mixture, for example by a standard extraction with a water immiscible solvent like 2-methyl-tetrahydrofuran, dichloromethane, methyl-tert.-butylether (MTBE), toluene, ethyl acetate, methyl-isobutylketone, benzene or isobutyl acetate, preferably dichloromethane or methyl-tert-butylether. Standard aqueous work-up procedures of the product-containing organic phase followed by switching the solvent to an antisolvent or using any of the techniques known to those skilled in the art allow the crystallisation of the compound of formula I. Alternatively, the desired product can be obtained by a chromatographic purification.

The potentially remaining amount of unreacted compounds of formulae VII and/or VIII in the reaction mixture can be recycled by alkaline hydrolysis with aqueous bases, for example sodium hydroxide (NaOH) or potassium hydroxide (KOH), in form of the respective 2-(2-hydroxy-5-nitrophenyl)-1-aryl-ethanones of formula IV

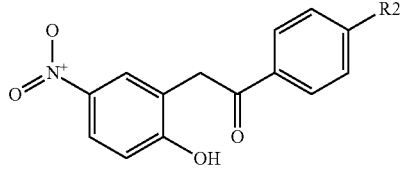

IV or the corresponding sodium or potassium salt of the formula V

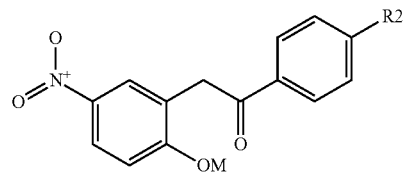

V wherein, in the compounds of the formulae IV and V R2 is as defined in formula I.

In the case that R2 is defined as 3-[dibutylamino]-propoxy the specific side chain in the para-position of the phenyl ring of Dronedarone is already incorporated in the compounds of the formulae I, IV, V, VII and VIII. When R2 is defined as mentioned above, but not as 3-[dibutylamino]-propoxy, the other para-substituents R2 either comprise protecting groups designated to be cleaved in a later stage of the synthesis sequence or they represent suitable leaving groups which activate the benzene nucleus and allow for the introduction of the 3-(dibutylamino)-propoxy group by nucleophilic substitution in a later step of the synthesis of Dronedarone.

Thus, the moieties in which R2 is OMe or OCH₂C₆H, are designated to be cleaved by dealkylation, according to methods well known in the literature, for example as described in the textbook by P. J. Kocienski, Protecting groups, Georg Thieme Verlag Stuttgart, New York 1994. After being liberated as the free hydroxyl function by any of the cleaving methods described there, the 3-(dibutylamino)-propoxy side chain of Dronedarone can be introduced by alkylation with 1-dibutylamino-3-chloropropane in presence of a base in an analogous fashion as described in WO0248078. On the other hand, the moieties in which R2 is defined as F, Cl or Br are replaced by means of nucleophilic substitution of the respective halide with 1-dibutylamino-3-hydroxypropane in the presence of a base. One typical procedure to achieve such substitution is given in Bioorganic & Medicinal Chemistry 12 (23), 6209-6219 (2004).

The invention further relates to a compound of the formula VII

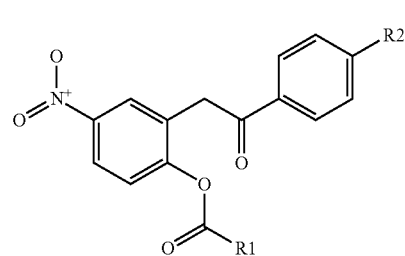

VII wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, OCH₂C₆H₅, F, Cl, Br or OCH₂CH₂CH₂N(CH₂CH₂CH₂CH₃)₂;
and salts thereof.

Another aspect of the invention is directed to the process for preparing a compound of the formula I

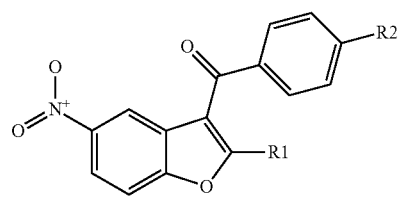

I wherein
R1 is alkyl having 1, 2, 3, 4, 5, 6, 7, 8, 9, 10, 11 or 12 carbon atoms or cycloalkyl having 3, 4, 5, 6 or 7 carbon atoms;

R2 is methoxy, OCH$_2$C$_6$H$_5$, F, Cl, Br or OCH$_2$CH$_2$CH$_2$N(CH$_2$CH$_2$CH$_2$CH$_3$)$_2$;
and salts thereof;
which comprises, as shown in scheme 5, Scheme 5

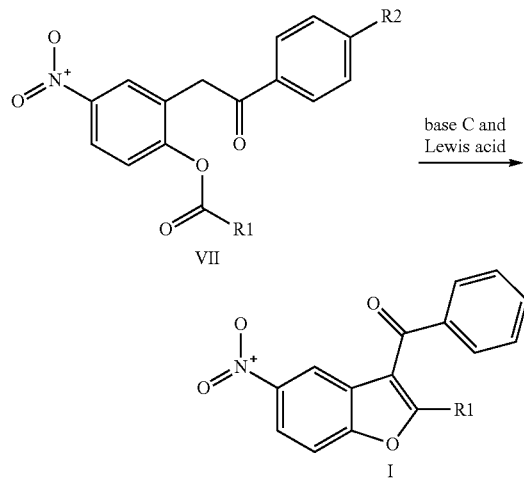

reacting a compound of the formula VII or a salt thereof with a base C and a Lewis acid,
wherein R1 and R2 in the compound of the formula VII are each as defined in formula I.

This process corresponds to step 2 of method 2 described above and comprises, therefore, the same reaction conditions as described above.

The invention further relates to a compound of the formula VIII

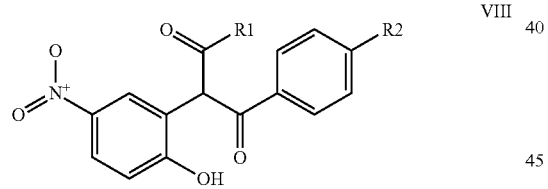

wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, OCH$_2$C$_6$H$_5$, F, Cl, Br or OCH$_2$CH$_2$CH$_2$N(CH$_2$CH$_2$CH$_2$CH$_3$)$_2$;
and salts thereof.

Another aspect of the invention is directed to the process for preparing a compound of the formula I

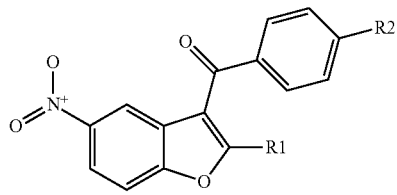

wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, OCH$_2$C$_6$H$_5$, F, Cl, Br or OCH$_2$CH7CH$_2$N(CH$_2$CH$_2$CH$_2$CH$_3$)$_2$;
and salts thereof;
which comprises, as shown in scheme 6, Scheme 6

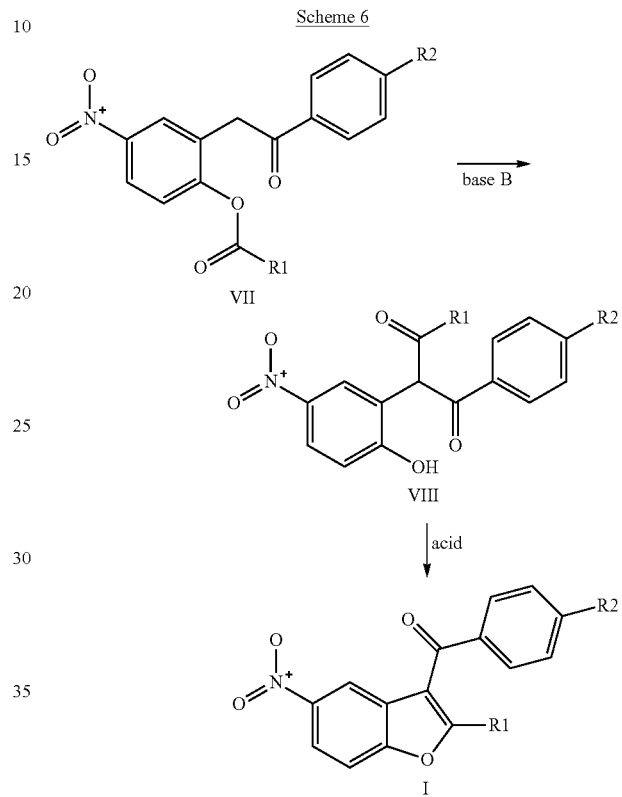

a) treatment of the ester of the formula VII with a base B providing the 1,3-diketone of the formula VIII;
b) heating of the 1,3-diketone of formula VIII in an acid providing the compound of the formula I;
wherein, in the compounds of the formulae VII and VIII R1 and R2 are each as defined in formula I.

This process corresponds to steps 2 and 3 of method 1 described above and comprises, therefore, the same reaction conditions as described above.

Another aspect of the invention is directed to the process for preparing a compound of the formula I

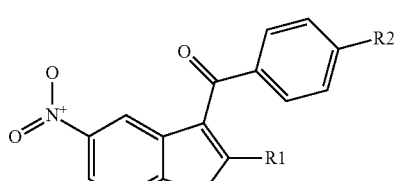

wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, OCH$_2$C$_6$H$_5$, F, Cl, Br or OCH$_2$CH$_2$CH$_2$N(CH$_2$CH$_2$CH$_2$CH$_3$)$_2$;

and salts thereof;
which comprises, as shown in scheme 7,

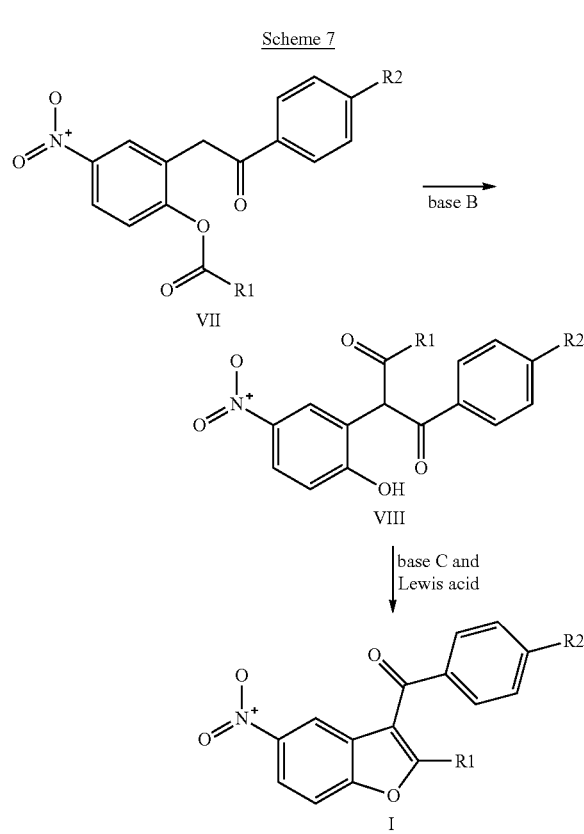

a) treatment of the ester of the formula VII with a base B providing the 1,3-diketone of the formula VIII;
b) transformation of the 1,3-diketone of the formula VIII into the compound of the formula I by using a base C in combination with a Lewis acid;

wherein, in the compounds of the formulae VII and VIII R1 and R2 are each as defined in formula I.

This process corresponds to steps 2 and 3 of method 3 described above and comprises, therefore, the same reaction conditions as described above.

Another aspect of the invention is directed to the process for preparing a compound of the formula VII

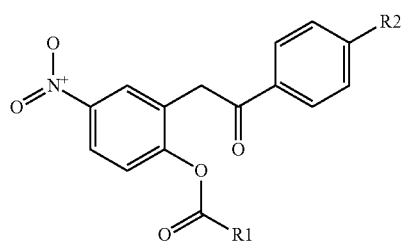

wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, OCH$_2$C$_6$H$_5$, F, Cl, Br or OCH$_2$CH$_2$CH$_2$N(CH$_2$CH$_2$CH$_2$CH$_3$)$_2$;
and salts thereof;
which comprises, as shown in scheme 8,

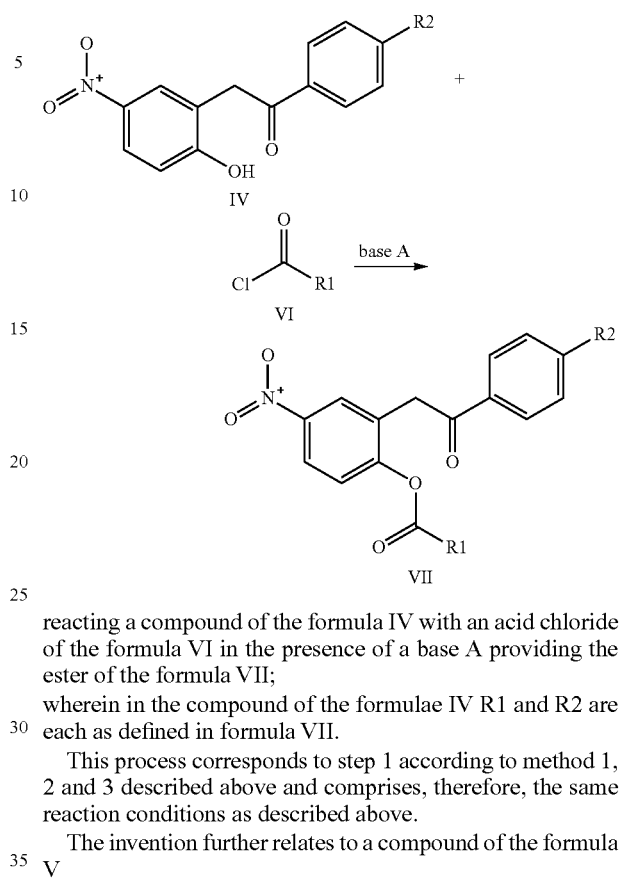

reacting a compound of the formula IV with an acid chloride of the formula VI in the presence of a base A providing the ester of the formula VII;
wherein in the compound of the formulae IV R1 and R2 are each as defined in formula VII.

This process corresponds to step 1 according to method 1, 2 and 3 described above and comprises, therefore, the same reaction conditions as described above.

The invention further relates to a compound of the formula V

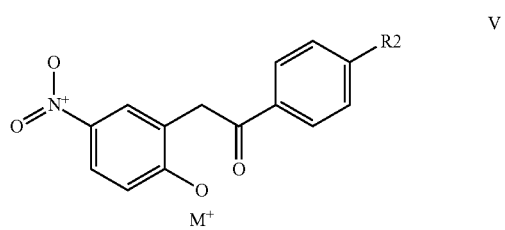

wherein
R2 is methoxy, OCH$_2$C$_6$H$_5$, F, Cl, Br or OCH$_2$CH$_2$CH$_2$N(CH$_2$CH$_2$CH$_2$CH$_3$)$_2$ and
M is Na or K.

Another aspect of the invention is directed to the process for preparing a compound of the formula VII

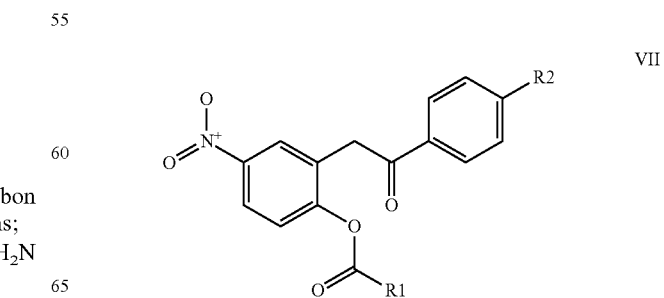

wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, $OCH_2C_6H_5$, F, Cl, Br or $OCH_2CH_2CH_2N(CH_2CH_2CH_2CH_3)_2$;
and salts thereof;
which comprises, as shown in scheme 9,

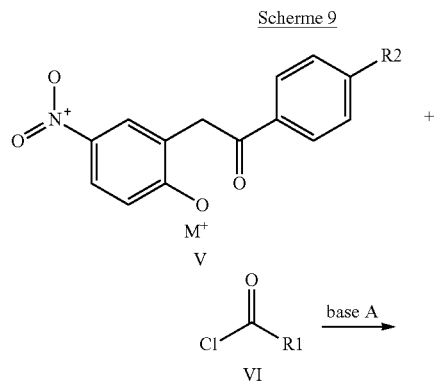

reacting a compound of the formula V with an acid chloride of the formula VI in the presence of a base A providing the ester of the formula VII;
wherein in the compound of the formulae IV R1 and R2 are each as defined in formula VII and M is Na or K.

The reaction conditions of this process are also described above in the reaction conditions for step 1 according to method 1, 2 or 3.

In one embodiment R1 in the compounds of formulae I, VI, VII and VIII is alkyl having 1, 2, 3, 4, 5, 6, 7, 8, 9, 10, 11 or 12 carbon atoms, for example alkyl having 1, 2, 3, 4, 5 or 6 carbon atoms, preferably n-butyl.

In another embodiment R2 in the compounds of formulae I, IV, V, VII and VIII is methoxy, F, Cl, Br or $OCH_2CH_2CH_2N(CH_2CH_2CH_2CH_3)_2$ (dibutylaminopropoxy), preferably methoxy, Cl or dibutylaminopropoxy.

In a preferred embodiment the compound of formula I is prepared according to a process described above, wherein R1 is n-butyl and R2 is methoxy.

In another preferred embodiment the compound of formula I is prepared according to a process described above, wherein R1 is n-butyl and R2 is Cl.

In another preferred embodiment the compound of formula I is prepared according to a process described above, wherein R1 is n-butyl and R2 is dibutylaminopropoxy.

If in the compounds of the formulae I and IV to VIII any groups, substituents, ring members, numbers or other features such as, for example, alkyl groups etc. occur several times, they can all independently of one another have any of the indicated meanings and can in each case be identical or different from one another.

When the compounds of the formulae and IV to VIII contain one or more centers of asymmetry, they may each independently have either S or R configuration, unless stated otherwise. The compounds of the formulae I and IV to VIII may be present in the form of optical isomers, of diastereomers, of racemates or of mixtures in all ratios thereof and in all possible tautomeric forms, unless they are more precisely defined. For example the compounds of the formula V may also be present as tautomers (keto or enol form) or as a mixture of tautomeric structures:

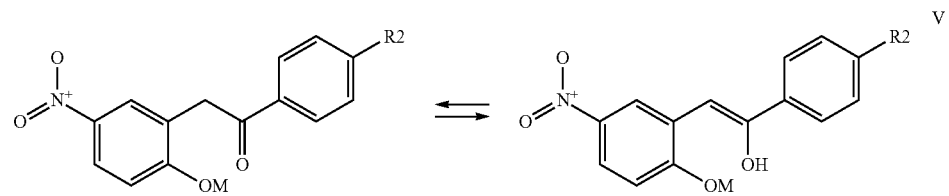

For the purpose of the present invention the compounds of the formulae I and IV to VIII can be used in form of all derivatives, for example solvates such as hydrates and alcohol adducts, of the formulae I and IV to VIII. The invention likewise encompasses all crystal modifications of the compounds of the formulae I and IV to VIII.

The above-described compounds of the formulae I, IV and VI to VIII may be used in the process according to the invention in the form of their salts or in salt free form and/or may be isolated in the form of their salts or in salt free form. Salts may be obtained by the customary methods, for example by reacting with acids or bases in a solvent, or by anion exchange or cation exchange from other salts. Useful acid addition salts are, for example, halides, in particular hydrochlorides and hydrobromides, lactates, sulfates, citrates, tartrates, acetates, phosphates, methylsulfonates, benzenesulfonates, p-toluenesulfonates, adipates, fumarates, gluconates, glutamates, glycerolphosphates, maleates, benzoates, oxalates and pamoates and trifluoroacetates. If the compounds of the formulae I, IV and VI to VIII contain an acid group, they are capable of forming salts with bases, for example as alkali metal salts, preferably sodium or potassium salts, or as ammonium salts, for example as salts with ammonia or organic amines or amino acids. They can also be present as zwitterions. In the case of the preparation of active ingredients, preference is given to physiologically tolerated salts and pharmaceutically acceptable salts.

Alkyl radicals may be straight-chain or branched. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl, hexyl, heptyl, octyl, nonyl, decyl, undecyl and dodecyl. Preferred alkyl radicals are methyl, ethyl, n-propyl, isopropyl and n-butyl, most preferred is n-butyl.

Examples of cycloalkyl radicals are cyclopropyl, cyclobutyl, cyclopentyl, cyclohexyl and cylcoheptyl. The cycloalkyl radicals may also be present branched as alkylcycloalkyl or cycloalkylalkyl.

Abbreviations:
ca. circa
DBU 1,8-diaza-bicyclo[5.4.0]-undec-7-ene
h hour(s)
i.vac. in vacuum
LC-MS liquid chromatography-mass spectrometry
Me methyl
MIBK methyl-isobutyl ketone
MTBE methyl-tert.-butylether
NMR Nuclear magnetic resonance
RP-HPLC reversed phase high performance liquid chromatography
THF tetrahydrofuran
TMG 1,1,3,3,-tetramethylguanidine

EXAMPLES

This invention is described in more detail by the examples that follow. These examples are designated to illustrate the invention, but do not limit its scope. Each step of the process described in the present invention may be operated either batch by batch or as a continuous process, or semicontinuous mode, and is scalable on larger amounts than described here.

The NMR assignments are for illustration only based on analysis of the one-dimensional $^1$H NMR spectra as done by those skilled in the art. A more detailed analysis of the spectra may lead to minor reassignments of some NMR peaks, which obviously does not change the overall assignment, All $^1$H NMR spectra are recorded on a 500 MHz instrument, shifts are relative to TMS in [ppm], the solvent is always DMSO-$d_6$.

Example 1

Synthesis of 2-(2-hydroxy-5-nitrophenyl)-1-(4-methoxyphenyl)-ethanone potassium salt (a compound of the formula V, M=K, R2=OMe)

10.0 g (34.8 mmol) of 2-(2-hydroxy-5-nitrophenyl)-1-(4-methoxyphenyl)-ethanone (a compound of the formula IV, R2=OMe), prepared according to literature procedures (as described in U.S. Pat. No. 3,657,350. U.S. Pat. No. 3,577,441, C. Majdik et al., Revista de Chimie 40 (6), 490-3 (1989) and 40 (8), 689-93 (1989) (Bukarest)), were dissolved in 100 ml of acetone and stirred with a solution of 2.53 g (18.3 mmol) of potassium carbonate in 20 ml of distilled water for 1 h at 40-50° C. The solvents were evaporated and the remaining yellow solid was dried i. vac. to yield 11.3 g (99.8%) of the title compound. LC-MS purity >98% (MH$^+$287).

The $^1$H NMR spectrum detected the presence of a mixture of keto- and enol-forms: 3.80, 3.78 (2s, OMe), 3.93 (s, CH2 keto-form), 5.97 (d, =CH enol-form).

Example 2

Synthesis of 2-(2-pentanoyloxy-5-nitrophenyl)-1-(4-methoxyphenyl)-ethanone (a compound of the formula VII, R1=n-butyl; R2=OMe)

4.23 g (35.0 mmol) of valeroyl chloride (a compound of the formula VI, R1=n-butyl) were added with cooling at −10° C. to 20° C. to a stirred suspension of 11.3 g (34.7 mmol) of 2-(2-hydroxy-5-nitrophenyl)-1-(4-methoxyphenyl)-ethanone potassium salt (example 1) in 50 ml of dry acetone. After 30 minutes the reaction was complete, as monitored by RP-HPLC, and the mixture was filtered through a layer of Celite to remove the precipitated potassium chloride. The solution was evaporated to dryness to give 9.23 g (98%) of a yellow oil which slowly crystallized while standing at room temperature.

$^1$H NMR (DMSO-$d_6$): 0.75 (t, 3H, CH$_3$), 1.20, 1.45 (2 m, 4H, CH$_2$CH$_2$), 2.45 (t, 2H, CH$_2$C=O ester), 3.87 (s, 3H, OMe), 4.50 (s, 2H, CH$_2$C=O ketone), 7.07 and 8.05 (2d, 4H, Ar—H), 7.47, 8.23, 835 (3 m, 3H, Ar—H).

LC-MS: MH$^+$372.

Example 3

Synthesis of 2-(2-hydroxy-5-nitrophenyl)-1-(4-methoxyphenyl)-1,3-heptandione (a compound of the formula VIII, R1=n-butyl; R2=OMe)

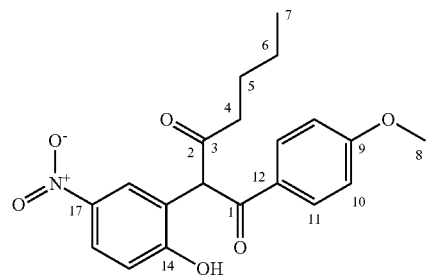 [SMILES: CCCCC(=O)C(C(=O)c1ccc(OC)cc1)c1cc([N+](=O)[O-])ccc1O]

Under argon atmosphere 6 ml (6.0 mmol) of a 1.0 M solution of lithium bis-(trimethylsilyl)-amide in dry THF were added at 5-10° C. to 2.00 g (5.38 mmol) of 2-(2-pentanoyloxy-5-nitrophenyl)-1-(4-methoxyphenyl)-ethanone (example 2) dissolved in 10 ml of dry tetraydrofuran (THF). After 20 minutes, the reaction was quenched with aqueous potassium dihydrogenphosphate buffer and the products were extracted with methyl-tert.-butylether. The title product was separated from unreacted starting material by reversed phase HPLC (RP-HPLC). The product containing fractions were pooled, dissolved in MTBE and washed with water. The organic phase was dried with sodium sulphate and the solvent was evaporated to give the title compound as a solid.

$^1$H NMR (DMSO-$d_6$): 0.82 (t, 3H, H-7), 1.25, 1.47 (2 m, 4H, H-5,6), 2.63 (m, 2H, H-4), 3.85 (s, 3H, H-8), 6.36 (s, 1H, H-2), 7.05 (2 m, 3H, Ar—H), 7.85 (m, 1H, Ar—H), 7.98, (m, 2H, Ar—H), 8.10 (m, 1H, Ar—H), 11.7 (s, 1H OH). $^{13}$C NMR (DMSO-$d_6$): 193.396 (C-1), 58.155 (C-2), 204.245 (C-3), 41.699 (C-4), 25.207 (C-5), 21.384 (C-6), 13.592(C-7), 55.575 (C-8), 163.688 (C-9), 121.639 (C-13), 161.059 (C-14), 139.257 (C-17).

LC-MS: MH$^+$372.

Example 4

Synthesis of 2-n-butyl-3-(4-methoxybenzoyl)-5-nitrobenzofuran (a compound of the formula I, R1=n-butyl, R2=OMe) using 1,1,3,3,-tetramethylguanidine (TMG) as base B (method 1)

2.00 g (5.38 mmol) of 2-(2-pentanoyloxy-5-nitrophenyl)-1-(4-methoxyphenyl)-ethanone (example 2) dissolved in 2 ml of dry toluene were treated under cooling at 15-25° C. with 0.815 g (7.07 mmol) of 1,1,3,3,-tetramethylguanidine (TMG). After stirring for ca. 20 min, the deep orange-red oil obtained was quickly transferred into 4.0 g (44.4 mmol) of methoxy-acetic acid under stirring at 75-85° C. The bright yellow solution was stirred at this temperature for further 10 hours until RP-HPLC analysis indicated the complete consumption of the intermediate 2-(2-hydroxy-5-nitrophenyl)-1-(4-methoxyphenyl)-1,3-heptandione (example 3). Then a hot solution of 5.6 g (85 mmol) of potassium hydroxide (85% KOH) in 20 ml of water was added under stirring at 70-90° C. and the stirring was continued for 15 minutes at that temperature. After cooling the mixture in an ice bath, 50 ml of MTBE were added under stirring and the recovered 2-(2-hydroxy-5-nitrophenyl)-1-(4-methoxyphenyl)-ethanone potassium salt (example 1) was separated by filtration, washed with water and dried (yield 0.52 g, 30%; LC-MS-purity >99%). The MTBE-phase was washed twice with 10 ml of aqueous 0.1 N KOH, then twice with 10 ml of aqueous 2 N HCl, dried over sodium sulphate and evaporated to dryness. The residue crystallized immediately to give 1.09 g of the title compound (57%; yield based on recovered starting material 81%);

$^1$H NMR (DMSO-$d_6$): 0.82 (t, 3H, $CH_3$), 1.25 and 1.68 (2 m, 4H, $CH_2CH_2$), 2.85 (t, 2H, $CH_2$), 3.87 (s, 3H, OMe), 7.15 and 7.85 (2d, 4H, Ar—H), 7.95 (m, 1H, Ar—H), 8.25 (m, 2H, Ar—H).

Purity by LC-MS >98% (MH$^+$354)

Example 5

Synthesis of 2-n-butyl-3-(4-methoxybenzoyl)-5-nitrobenzofuran (a compound of the formula I, R1=n-butyl, R2=OMe) using 2-tert.-butyl-1,1,3,3,-tetramethylguanidine as base B (method 1)

Under argon atmosphere 2.96 g (17.27 mmol, 1.2 equivalents) of 2-tert.-butyl-1,1,3,3,-tetramethylguanidine were added at 5-15° C. to 5.30 g (14.27 mmol) of 2-(2-pentanoyloxy-5-nitrophenyl)-1-(4-methoxyphenyl)-ethanone (example 2) dissolved in 4 ml of dry 2-methyl-tetrahydrofuran. After 15 min the deep orange-red oil was quickly transferred into 10.4 g (114 mmol) of methoxy-acetic acid under stirring at 75-85° C. The bright yellow solution was stirred at this temperature for further 12 hours until RP-HPLC analysis revealed the complete consumption of the intermediate 1,3-diketone (example 3). Then a hot solution of 14 g (0.20 mol) of potassium hydroxide (85% KOH) in 50 ml of water was added under stirring at 70-80° C. and the stirring was continued for 5 minutes at that temperature.

After cooling the mixture with an ice bath to room temperature 100 ml of MTBE were added under stirring. Only a small amount of 2-(2-hydroxy-5-nitrophenyl)-1-(4-methoxyphenyl)-ethanone potassium salt (example 1) was recovered by filtration (0.1 g, 2%). The MTBE-phase was washed twice with 20 ml of aqueous 0.1 N KOH, then twice with 20 ml of aqueous 2 N HCl, dried over sodium sulphate and evaporated to dryness. The residue crystallized immediately to yield 3.6 g (71%) of the title compound.

Example 6

Synthesis of 2-n-butyl-3-(4-methoxybenzoyl)-5-nitrobenzofuran (a compound of the formula I, R1=n-butyl, R2=OMe) using using 1,8-diazabicyclo[5.4.0]undec-7-ene (DBU) as base B (method 1)

Under argon atmosphere 0.62 g (4.1 mmol, 1.5 equivalents) of 1,8-diaza-bicyclo[5.4.0]-undec-7-ene (DBU) were added at 5-15° C. to 1.0 g (2.69 mmol) of 2-(2-pentanoyloxy-5-nitrophenyl)-1-(4-methoxyphenyl)-ethanone (example 2) dissolved in 7 ml of dry methyl-isobutyl ketone (MIBK). After stirring for ca. 15 min the deep orange-red oil was quickly transferred to 5 ml of acetic acid (83 mol) under stirring at 75-85° C. The bright yellow solution was stirred at this temperature for further 21 hours until RP-HPLC analysis indicated the complete consumption of the intermediate 1,3-diketone (example 3). Then 15 ml of aqueous 2 N NaOH were added, and stirring at 70-80° C. was continued for further 10 minutes. After cooling the mixture to room temperature, the product was extracted with 50 ml of MTBE. The organic phase was washed twice with 20 ml of aqueous 1 N NaOH, then twice with 20 ml of aqueous 2 N HCl, dried over sodium sulphate and evaporated to dryness. The residue immediately crystallized to yield 0.65 g (68%) of the title compound.

Example 7

Synthesis of 2-(2-hydroxy-5-nitrophenyl)-1-(4-chlorophenyl)-ethanone sodium salt (a compound of the formula V, M=Na, R2=Cl)

3.00 g (10.2 mmol) of 2-(2-hydroxy-5-nitrophenyl)-1-(4-chlorophenyi)-ethanone (a compound of the formula IV, $R^2$=Cl), prepared according to literature procedures (as described in U.S. Pat. Nos. 3,657,350; 3,577,441; C. Majdik et al., Revistade Chimie 40 (6), 490-3 (1989) and 40 (8), 689-93 (1989) (Bukarest)), were dissolved in 10 ml of dry acetone and stirred with a solution of 0.61 g (0.55 mmol) of sodium carbonate in 5 ml of distilled water for 1 h at 40-50° C. The solvents were evaporated and the yellow solid remaining was dried i. vac, to yield 3.2 g (99%) of the title compound.

LC-MS: MH$^+$291.

The $^1$H NMR spectrum detected the presence of a mixture of keto- and enol-forms: 4.20 (s, CH2 keto-form), 6.20 (d, =CH enol-form).

Example 8

Synthesis of 2-(2-pentanoyloxy-5-nitrophenyl)-1-(4-chlorophenyl)-ethanone (compound of the formula VII, R1=n-butyl; R2=Cl)

1.32 g (10.7 mmol) of valeroyl chloride (a compound of the formula VI, R1=n-butyl) were added with cooling at –10° C. to 20° C. to a stirred suspension of 3.2 g (10.2 mmol) of 2-(2-hydroxy-5-nitrophenyl)-1-(4-chlorophenyl)-ethanone sodium salt (example 7) in 20 ml of dry acetone. After 30 min the reaction was complete as confirmed by RP-HPLC and the mixture was filtered through a layer of Celite to remove the precipitated sodium chloride. The solution was evaporated to dryness to give 3.8 g (98%) of the pure product as a yellow solid.

$^1$H NMR (DMSO-$d_6$): 0.75 (t, 3H, $CH_3$), 1.20, 1.45 (2 m, 4H, $CH_2CH_2$), 2.45 (t, 2H, $CH_2$C=O ester), 3.87 (s, 3H, OMe), 4.58 (s, 2H, $CH_2$), 7.67 and 8.08 (2d, 4H, Ar—H), 7.47, 8.23, 8.35 (3 m, 3H, Ar—H).

LC-MS: MH$^+$376

Example 9

Synthesis of 2-n-butyl-3-(4-chlorobenzoyl)-5-nitrobenzofuran (a compound of the formula I, R1=n-butyl, R2=Cl) using 2-tert.-butyl-1,1,3,3,-tetramethylguanidine as base B (Method 1)

Under argon atmosphere 0.55 g (3.22 mol, 1.2 equivalents) of 2-tert.-butyl-1,1,3,3,-tetramethyl-guanidine were added at 5-15° C. to 1.00 g (2.66 mmol) of 2-(2-pentanoyloxy-5-nitrophenyl)-1-(4-chlorophenyl)-ethanone (example 8) dissolved in 4 ml of dry dichloromethane, After 15 min the deep orange-red oil was quickly transferred into 1.94 g (21.3 mmol) of methoxy-acetic acid under stirring at 75-85° C. The bright yellow solution was further stirred at this temperature over night until RP-HPLC analysis confirmed the complete conversion of the intermediate 1,3-diketone (a compound of the formula VIII wherein R1=n-butyl and R2=Cl; LC-MS: MH$^+$376). Then a solution of 2 g KOH in 15 ml water was added under stirring at 70-80° C., and stirring was continued for 10 minutes at that temperature. After cooling the mixture to room temperature, the product was extracted with 50 ml of MTBE. The organic phase was washed twice with 20 ml of aqueous 1 N NaOH, then twice with 20 ml of aqueous 2 N HCl, dried over sodium sulphate and evaporated to dryness. The residue immediately crystallized to yield 0.65 g (68%) of the title compound.

$^1$H NMR (DMSO-d$_6$): 0.80 (t, 3H, CH$_3$), 1.25 and 1.68 (2 m, 4H, CH$_2$CH$_2$), 2.83 (t, 2H, CH$_2$), 7.68 and 7.85 (2d, 4H, Ar—H), 7.96 (d, 1H, Ar—H), 8.28 (m, 2H, Ar—H).

LC-MS: MH$^+$358

Example 10

Synthesis of 2-n-butyl-3-(4-[3-(dibutylamino)-propoxyl-benzoyl)-5-nitrobenzofuran (a compound of the formula I, R1=n-butyl, R2=3-[dibutylamino]-propoxy) using 2-tert.-butyl-1,1,3,3,-tetramethylguanidine as base B (method 1)

a) 4-[3-(dibutylamino)-propoxy]-acetophenone was prepared from 4-fluoro-acetophenone, 3-dibutylamino-propanol and sodium hydride by the procedure described in J. Med. Chem., 12, 6209-6219, 2004. This acetophenone derivative was then transformed into 2-(2-hydroxy-5-nitrophenyl)-1-(4-[3-(dibutylamino)-propoxy]-phenyl)-ethanone (a compound of the formula IV, R2=3-[dibutylamino]-propoxy) in analogy to the procedures described in the literature (U.S. Pat. No. 3,657,350; U.S. Pat. No. 3,577,441; C. Majdik et al., Revistade Chimie 40 (6), 490-3 (1989) and 40/8). 689-93 (1989) (Bukarest)). Subsequent acylation with valeroyl chloride (a compound of the formula VI, R1=n-butyl) analogously as described in example 2 provided the 2-(2-pentanoyloxy-5-nitrophenyl)-1-(4-[3-(dibutylamino)-propoxyl-phenyly-ethanone (a compound of the formula VII, R1=n-butyl; R2=3-[dibutylamino]-propoxy].

b) 1.60 g (3.04 mmol) 2-(2-pentanoyloxy-5-nitrophenyl)-1-(4-[3-(dibutylamino)-propoxy]-phenyl)-ethanone (a compound of the formula VII, R1=n-butyl; R2=3-[dibutylamino]-propoxy] dissolved in 4 ml of d dichloromethane were treated under cooling at 15-25° C. with 0.57 g (3.34 mmol) of 2-tert.-butyl-1,1,3,3,-tetramethyl-guanidine. After 15 min the deep orange-red oil was quickly transferred into 2.21 g (24.3 mmol) of methoxy-acetic acid under stirring at 75-85° C. The bright yellow solution was stirred at this temperature for further 12 hours until RP-HPLC analysis confirmed the complete consumption of the intermediate 2-(2-hydroxy-5-nitrophenyl)-1-(4-[3-(dibutylamino)-propoxy]-phenyl)-1,3-heptandione (compound of the formula VIII wherein R1 is n-butyl and R2 is 3-[dibutylamino]-propoxy, LC-MS: MH$^+$527). Then a hot solution of 3.12 g (47.3 mmol) of potassium hydroxide (85% KOH) in 20 ml of water was added under stirring at 70-90° C. and the stirring was continued for 10 minutes at that temperature. After cooling to room temperature the mixture was extracted with dichloromethane. The organic phase was washed with diluted aqueous NaOH, aqueous potassium dihydrogen phosphate buffer and brine, and then evaporated to dryness. The residue was purified by flash chromatography on silica gel by quick filtration with ethyl acetate as eluent to give 0.80 g (52%) of the title compound as a yellow oil.

$^1$H NMR (DMSO-d$_6$): 0.82 (3t, 9H, CH$_3$), 1.20-1.40 (m, 10H, CH$_2$), 1.68 (m, 2H, 2-butylCH$_2$), 1.85 (m, 2H, OCH$_2$CH$_2$CH$_2$N), 2.35 (m, 4H, CH$_2$N), 2.53 (m, 2H, OCH$_2$CH$_2$CH$_2$N), 2.84 (t, 2H, Ar—CH$_2$), 4.13 (t, 2H OCH$_2$), 7.08 and 7.80 (2d, 4H, Ar—H), 7.93 (m, 1H, Ar—H), 8.25 (m, 2H, Ar—H).

LC-MS: MH$^+$509

Example 11

Synthesis of 2-n-butyl-3-(4-methoxybenzoyl)-5-nitrobenzofuran (a compound of the formula I, R1=n-butyl, R2=OMe) using titanium-tetrachloride (method 2)

Under argon atmosphere 30 ml (30 mmol, 1.1 equivalents) of a 1 M solution of TiCl$_4$ in dichloromethane were added at −10° C. to 0° C. to 10.0 g (26.9 mmol) of 2-(2-pentanoyloxy-5-nitrophenyl)-1-(4-methoxyphenyl)-ethanone (example 2) dissolved in 15 ml of dry dichloromethane and 5.45 g (53.9 mmol, 2 equivalents) of triethylamine. After stirring the mixture at 38-39° C. for about 2 days, the reaction mixture was diluted with 50 ml of 1 N aqueous HCl and 50 ml of MTBE. The organic phase was separated and washed with 30 ml of 1 N aqueous HCl, 30 ml of aqueous saturated sodium bicarbonate solution and brine, dried over sodium sulphate and evaporated to dryness. The residue crystallized to yield 9.4 g (99%) of the title compound.

Example 12

Synthesis of 2-n-butyl-3-(4-methoxybenzoyl)-5-nitrobenzofuran (a compound of the formula 1, R1=n-butyl, R2=OMe) using zinc chloride (method 2)

Under argon atmosphere 15.4 ml (15.4 mmol, 1.1 equivalent) of a 1 M solution of ZnCl$_2$ in diethylether were added at 0-10° C. to 5.21 g (14.0 mmol) of 2-(2-pentanoyloxy-5-nitrophenyl)-1-(4-methoxyphenyl)-ethanone (example 2) dissolved in 15 ml of dry dichloromethane and 2.13 g (21.0 mmol, 1.5 equivalents) of triethylamine. After stirring the mixture at 38-39° for about 16 hours, the reaction mixture was diluted with 50 ml of 1 N aqueous HCl and 30 ml of MTBE. The organic phase was separated and washed thoroughly with 2 N aqueous NaOH at 40° C. for 20 minutes, then with 20 ml of 1 N aqueous HCl at room temperature and brine, dried over sodium sulphate and evaporated to dryness. The residue crystallized to yield 3.50 g (71%) of the title compound.

Example 13

One-pot-synthesis of 2-n-butyl-3-(4-methoxybenzoyl)-5-nitrobenzofuran (a compound of the formula 1, R1=n-butyl, R2=OMe) from the potassium salt (example 1) using titanium tetrachloride (method 2)

0.23 g (1.89 mmol, 1.1 equivalents) of valeroyl chloride (a compound of the formula V, R2=n-butyl) were added at room temperature to a stirred suspension of 0.56 g (1.72 mmol) of 2-(2-hydroxy-5-nitrophenyl)-1-(4-methoxyphenyl)-ethanone potassium salt (example 1) in 10 ml of dry dichloromethane. After 14 hours 0.21 g (2.07 mmol, 1.2 equivalents) of triethylamine and then 1.89 ml of a 1 M solution of TiCl$_4$ in dichloromethane (1.89 mmol, 1.1 equivalents) were added. After stirring the mixture at 40° C. over night LC-MS analysis confirmed nearly complete conversion. The reaction mixture was diluted with 10 ml of 1 N aqueous HCl and 30 ml of MTBE. The organic phase was separated and washed thoroughly with 2 N aqueous NaOH at 40° C. for 20 minutes, then with 10 ml of 1 N aqueous HCl at room temperature and brine, dried over sodium sulphate and evaporated to dryness. The residue crystallized to give 0.48 g (79%) of the title compound.

Example 14

Synthesis of 2-n-butyl-3-(4-chlorobenzoyl)-5-nitrobenzofuran (compound of the formula 1, R1=n-butyl, R2=Cl) using titanium tetrachloride (method 2)

Under argon atmosphere 0.28 g (2.13 mol, 2 equivalents) of diisopropylethylamine and 1.3 ml (1.3 mmol, 1.2 equivalents) of a 1M solution of TiCl$_4$ in dichloromethane were added at −15° C. to 0.40 g (1.06 mmol) of 2-(2-pentanoyloxy-5-nitrophenyl)-1-(4-chlorophenyl)-ethanone (example 8) dissolved in 5 ml of dry 1,2-dichloroethane. After heating the mixture for 4 h at 80° C., LC-MS analysis confirmed complete conversion. The reaction mixture was diluted with 5 ml of 1 N aqueous HCl and 30 ml of MTBE. The organic phase was separated and washed thoroughly with 2 N aqueous NaOH at 40° C. for 20 minutes, then with 10 ml of 1 N aqueous HCl at room temperature and brine, dried over sodium sulphate and evaporated to dryness. The residue crystallized to give 0.34 g (89%) of the title compound.

Example 15

Synthesis of 2-n-butyl-3-(4-methoxybenzoyl)-5-nitrobenzofuran (a compound of the formula 1, R1=n-butyl, R2=OMe) (method 3)

Under argon atmosphere 0.56 g (3.26 mmol, 1.2 equivalents) of 2-tert.-butyl-1,1,3,3,-tetramethylguanidine were added at 5-15° C. to 1.00 g (2.69 mmol) of 2-(2-pentanoyloxy-5-nitrophenyl)-1-(4-methoxyphenyl)-ethanone (example 2) dissolved in 5 ml of dry dichloromethane. After stirring for 20 min, 20 ml of 0.5 M aqueous HCl solution and 50 ml of MTBE were added. The organic phase was dried with sodium sulphate and evaporated to give quantitatively the crude 2-(2-hydroxy-5-nitrophenyl)-1-(4-methoxyphenyl)-1,3-heptanedione (a compound of the formula VIII, R1=n-butyl; R2=OMe) which was further purified by RP-chromatography to yield 0.7 g (70%) of the pure material. This 1,3-diketone was reacted with 0.38 g of triethylamine (3.8 mmol, 2 equivalents) and 0.44 g of TiCl$_4$ (2.2 mmol, 1.2 equivalents) in dichloromethane exactly as described in example 11 to give 0.65 g (98% based on 1,3-diketone) of the title compound.

Example 16

Synthesis of 2-n-butyl-3-(4-methoxybenzoyl)-5-nitrobenzofuran (a compound of the formula I, R1=n-butyl, R2=OMe) using tetramethylammonium acetate as base B (method 1)

Under argon atmosphere 1.60 g (4.31 mmol) of 2-(2-pentanoyloxy-5-nitrophenyl)-1-(4-methoxyphenyl)-ethanone (example 2) and 0.80 g (5.41 mmol; 1.25 equivalents) of tetramethylammonium acetate (90% technical grade) were stirred for 2 hours at room temperature. The deep orange-red solution was quickly transferred into 5.0 g (83 mmol) of acetic acid under stirring at 85° C. The bright yellow solution was further stirred at this temperature for 14 hours. The mixture was evaporated to a yellow oil and treated with a hot solution of 3.0 g (45 mmol) of potassium hydroxide (85% KOH) in 10 ml of water for 15 minutes. After dilution with 30 ml of MTBE and 20 ml of cold water, the precipitated 2-(2-hydroxy-5-nitrophenyl)-1-(4-methoxyphenyl)-ethanone potassium salt (example 1) was recovered by filtration (yield 0.30 g, 21%). The MTBE-phase was washed twice with 10 ml of aqueous 0.1 N NaOH, then twice with 10 ml of aqueous 2 N HCl, dried over sodium sulphate and evaporated to dryness. The residue crystallized from methanol to give 0.80 g of the title compound (yield 53% and 67% based on the recovered starting material).

Example 17

Synthesis of 2-n-butyl-3-(4-methoxybenzoyl)-5-nitrobenzofuran (a compound of the formula 1, R1=n-butyl, R2=OMe) using aluminium chloride (method 2)

Under argon atmosphere 0.51 g (1.37 mmol) of 2-(2-pentanoyloxy-5-nitrophenyl)-1-(4-methoxyphenyl)-ethanone (example 2), 0.44 g (3.30 mmol) of aluminium chloride (AlCl$_3$) and 0.41 g (4.00 mmol) of triethylamine in 4 ml of dry 1,2-dichlorethane were stirred for 48 hours at 90° C. The mixture was taken up in 5 ml of 1 N HCl and 10 ml of MTBE, the organic phase washed with water and brine, dried over sodium sulphate and evaporated to give the title compound as a yellow oil (yield 0.45 g, 93%) which immediately crystallized.

Example 18

Synthesis of 2-n-butyl-3-(4-methoxybenzoyl)-5-nitrobenzofuran (a compound of the formula I, R1=n-butyl, R2=OMe) using 1-butyl-3-methyl-imidazolium valerate or 1-butyl-3-methyl-imidazolium acetate as base B (method 1)

The valerate salt was prepared in analogy to the procedures described in the examples 1 and 6 in the patent publication WO2006021304 using valeric acid instead of acetic acid. Under argon atmosphere 3.00 g (8.08 mmol) of 2-(2-pentanoyloxy-5-nitrophenyl)-1-(4-methoxyphenyl)-ethanone (example 2) were added to 2.00 g (8.00 mmol) of 1-butyl-3-methyl-imidazolium valerate at 75° C. After stirring the solution for 2 hours at this temperature, the mixture was combined with 3 ml of acetic acid, stirred for 1 hour at this temperature, cooled to room temperature and quenched with 10 ml of water and 20 ml of MTBE. The organic phase was washed once with 10 ml of water and 10 ml of brine, dried over MgSO$_4$ and concentrated to dryness. The crude material was purified by flash chromatography on silica (heptane/acetic acid as eluent) to give 1.36 g (48%) of the crystalline title compound.

The reaction was also carried out using 0.14 g (0.59 mmol) of the commercially available 1-butyl-3-methyl-imidazolium acetate with 0.11 g (0.29 mmol) of 2-(2-pentanoyloxy-5-nitrophenyl)-1-(4-methoxyphenyl)-ethanone (example 2) under the same reaction conditions as described in example 18. By comparing the LC-MS chromatogram of the crude reaction mixture with the chromatogram obtained from the reaction with 1-butyl-3-methyl-imidazolium valerate it was concluded that both methods delivered the targed compound in similar yield.

Example 19

Synthesis of 2-n-butyl-3-(4-methoxybenzoyl)-5-nitrobenzofuran (a compound of the formula I, R1=n-butyl, R2=OMe) using iron-trichloride (method 2)

A flask equipped with a Dean-Stark condenser was charged with 20 ml of dry toluene, 2.00 g (10.7 mmol, 2 equivalents) of tri-n-butylamine, 2.00 g (5.39 mmol) of 2-(2-pentanoyloxy-5-nitrophenyl)-1-(4-methoxyphenyl)-ethanone (example 2) and 0.05 g (0.30 mmol, 0.05 equivalents) of anhydrous FeCl₃. The mixture was kept at reflux temperature while some toluene was removed during the reaction. After 2.5 hours RP-HPLC analysis confirmed the quantitative conversion of the starting compound into the title compound. The mixture was taken up in 20 ml of 1 N HCl and 20 ml of MTBE, the organic phase was washed with water and brine, dried over sodium sulphate and evaporated to give the title compound (yield: 1.90 g, 99%).

Example 20

Synthesis of 2-n-butyl-3-(4-methoxybenzoyl)-5-nitrobenzofuran (a compound of the formula 1, R1=n-butyl, R2=OMe) using manganese-dichloride (method 2)

A flask equipped with a Dean-Stark condenser was charged with 20 ml of dry toluene, 2.00 g (10.7 mmol, 2 equivalents) of tri-n-butylamine, 2,00 g (5.39 mmol) of 2-(2-pentanoyloxy-5-nitrophenyl)-1-(4-methoxyphenyl)-ethanone (example 2) and 0.06 g (0.47 mmol, 0.04 equivalents) of anhydrous MnCl₂. The mixture was kept at reflux temperature while some toluene was removed during the reaction, After 2.5 hours RP-HPLC analysis confirmed the quantitative conversion of the starting compound into the title compound. The mixture was taken up in 20 ml of 1 N HCl and 20 ml of MTBE, the organic phase was washed with water and brine, dried over sodium sulphate and evaporated to give the title compound (yield: 1.90 g, 99%).

The invention claimed is:

1. A compound of formula VII,

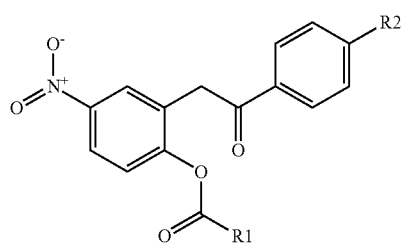

wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, OCH₂C₆H₅, F, Cl, Br or OCH₂CH₂CH₂N(CH₂CH₂CH₂CH₃)₂;
and salts thereof.

2. A process for preparing a compound of the formula I

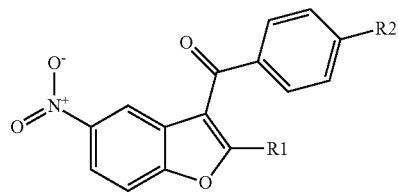

wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, OCH₂C₆H₅, F, Cl, Br or OCH₂CH₂CH₂N(CH₂CH₂CH₂CH₃)₂;
and salts thereof;
which comprises

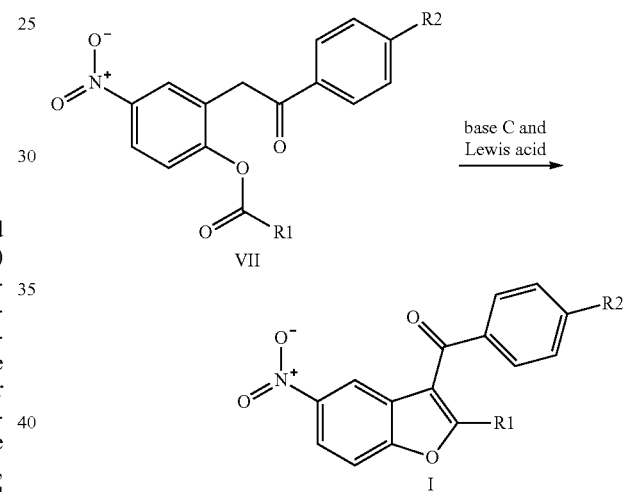

reacting a compound of the formula VII with a base C and a Lewis acid,
wherein R1 and R2 in the compound of the formula VII are each as defined in formula I, wherein base C is selected from the group consisting of triethylamine, tri-n-butylamine, tri-n-propylamine, N-methylimidazol, diisopropylethylamine, and sparteine.

3. A process claimed in claim 2 wherein
the Lewis acid is titanium-tetrachloride (TiCl₄), aluminium-chloride (AlCl₃), zinc-chloride (ZnCl₂), zinc-bromide (ZnBr₂), iron-chlorides (FeCl₂ and FeCl₃), iron-acetylacetonates (Fe[acac]₂ and Fe[acac]₃), iron-acetates (Fe[OAc]₂) and Fe[OAc]₃), manganese-dichloride (MnCl₂), manganese-dibromide (MnBr₂), manganese-acetates (Mn[OAc]₂ and Mn[OAc]₃), manganese-acetylacetonates (Mn[acac]₃ and Mn[acac]₂), zirconium-tetrachloride (ZrCl₄), scandium triflate (Sc[OSO₂CF₃]₃), scandium-trichloride (ScCl₃), tin-tetrachloride (SnCl₄), bismuth-triflate (Bi[OSO₂CF₃]₃), indium-triflate (In[OSO₂CF₃]₃), and cerium-trichloride (CeCl₃).

4. A compound of the formula VIII

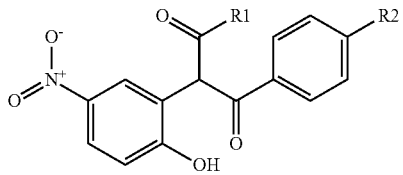

wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, $OCH_2C_6H_5$, F, Cl, Br or $OCH_2CH_2CH_2N(CH_2CH_2CH_2CH_3)_2$;
and salts thereof.

5. A process for preparing a compound of the formula I

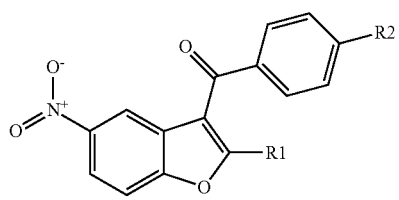

wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, $OCH_2C_6H_5$, F, Cl, Br or $OCH_2CH_2CH_2N(CH_2CH_2CH_2CH_3)_2$;
and salts thereof;
which comprises

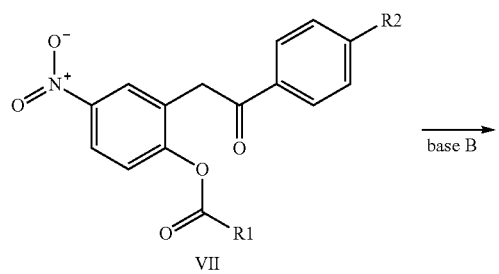

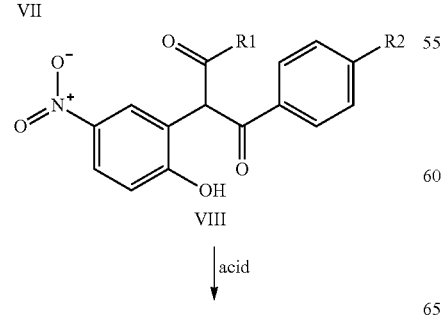

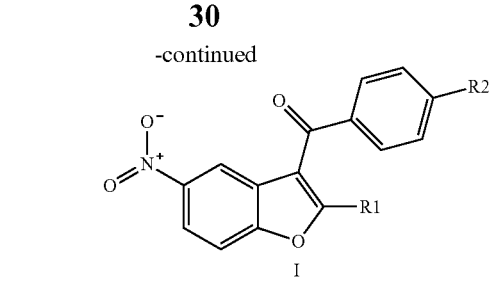

a) treatment of the ester of the formula VII with a base B providing the 1,3-diketone of the formula VIII;
b) heating of the 1,3-diketone of formula VIII in an acid providing the compound of the formula I;
wherein, in the compounds of the formulae VII and VIII R1 and R2 are each as defined in formula I,
wherein base B is selected from the group consisting of potassium-carbonate, sodium-carbonate, cesium-carbonate, sodium-hydride, potassium-hydride, lithium-bis(trimethylsilyl)amide, potassium-bis(trimethylsilyl)amide, sodium- or potassium-tert-butoxide, sodium- or potassium-tert.-pentoxide, lithium-diisopropylamide, tetraalkylammonium-hydroxide or -acetate wherein alkyl in each alkyl residue is independently of each other methyl, ethyl, propyl, butyl or decyl and wherein one or more alkyl residues can be replaced by benzyl, a 1,3-dialkyl-imidazolium carboxylate, wherein each alkyl residue is independently of each other methyl, ethyl, propyl or butyl and wherein carboxylate is acetate, propionate butyrate, pivaloate or valerate, 1,1,3,3,-tetramethyl-guanidine, 2-tert.-butyl-1,1,3,3,-tetramethyl-guanidine, 1,1,2,3,3-pentamethylguanidine, 1,5-diazabicyclo[4.3.0]non-5-ene, 1,8-diazabicyclo[5.4.0]undec-7-ene, 7-methyl-1,5,7-triazabicyclo[4.4.0]dec-5-ene, 1,5,7-triazabicyclo[4.4.0]dec-5-ene and 2-tert.-butylimino-2-diethylamino-1,3-dimethyl-perhydro-1,3,2-diazaphosphorine.

6. A process as claimed in claim 5 wherein
the acid is acetic acid, 2-chloro-acetic acid, methoxy-acetic acid, propionic acid, butyric acid, valeric acid or pivalic acid or a mixture of at least 2 of aforesaid acids.

7. A process as claimed in claim 5 wherein the compound of the formula VIII is isolated and then is reacted with an acid.

8. A process as claimed in claim 5 wherein the compound of the formula VIII is prepared in situ without being isolated and then is reacted with an acid.

9. A process for preparing a compound of the formula I

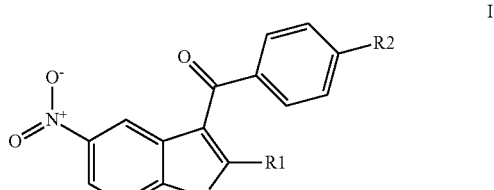

wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, $OCH_2C_6H_5$, F, Cl, Br or $OCH_2CH_2CH_2N(CH_2CH_2CH_2CH_3)_2$;
and salts thereof;

which comprises

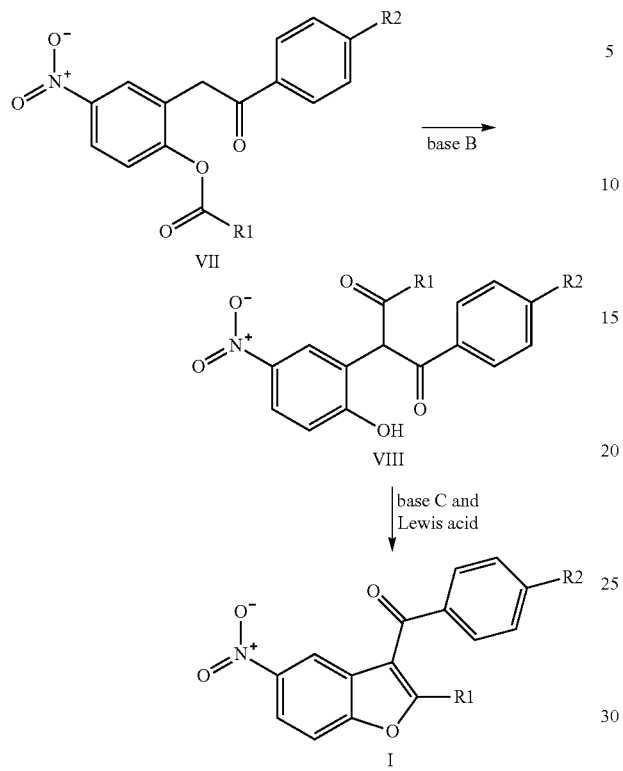

a) treatment of the ester of the formula VII with a base B providing the 1,3-diketone of the formula VIII;
b) transformation of the 1,3-diketone of the formula VIII into the compound of the formula I by using a base C in combination with a Lewis acid;
wherein, in the compounds of the formulae VII and VIII R1 and R2 are each as defined in formula I,
wherein base B is selected from the group consisting of potassium-carbonate, sodium-carbonate, cesium-carbonate, sodium-hydride, potassium-hydride, lithium-bis(trimethylsilyl)amide, potassium-bis(trimethylsilyl) amide, sodium- or potassium-tert-butoxide, sodium- or potassium-tert.-pentoxide, lithium-diisopropylamide, tetraalkylammonium-hydroxide or -acetate wherein alkyl in each alkyl residue is independently of each other methyl, ethyl, propyl, butyl or decyl and wherein one or more alkyl residues can be replaced by benzyl, a 1,3-dialkyl-imidazolium carboxylate, wherein each alkyl residue is independently of each other methyl, ethyl, propyl or butyl and wherein carboxylate is acetate, propionate butyrate, pivaloate or valerate, 1,1,3,3,-tetramethyl-guanidine, 2-tert.-butyl-1,1,3,3,-tetramethyl-guanidine, 1,1,2,3,3-pentamethylguanidine, 1,5-diazabicyclo[4.3.0]non-5-ene, 1,8-diazabicyclo[5.4.0]undec-7-ene, 7-methyl-1,5,7-triazabicyclo[4.4.0]dec-5-ene, 1,5,7-triazabicyclo[4.4.0]dec-5-ene and 2-tert.-butylimino-2-diethylamino-1,3-dimethyl-perhydro-1,3,2-diazaphosphorine, and wherein base C is selected from the group consisting of triethylamine, tri-n-butylamine, tri-n-propylamine, N-methylimidazol, diisopropylethylamine and sparteine.

10. A process as claimed in claim 9 wherein the Lewis acid is titanium-tetrachloride (TiCl$_4$), aluminium-chloride (AlCl$_3$), zinc-chloride (ZnCl$_2$), zinc-bromide (ZnBr$_2$), iron-chlorides (FeCl$_2$ and FeCl$_3$), iron-acetylacetonates (Fe[acac]$_2$ and Fe[acac]$_3$), iron-acetates (Fe[OAc]$_2$ and Fe[OAc]$_3$), manganese-dichloride (MnCl$_2$), manganese-dibromide (MnBr$_2$), manganese-acetates (Mn[OAc]$_2$ and Mn[OAc]$_3$), manganese-acetylacetonates (Mn[acac]$_3$ and Mn[acac]$_2$), zirconium-tetrachloride (ZrCl$_4$), scandium triflate (Sc[OSO$_2$CF$_3$]$_3$), scandium-trichloride (ScCl$_3$), tin-tetrachloride (SnCl$_4$), bismuth-triflate (Bi[OSO$_2$CF$_3$]$_3$), indium-triflate (In[OSO$_2$CF$_3$]$_3$), and cerium-trichloride (CeCl$_3$).

11. A process as claimed in claim 9 wherein the compound of the formula VIII is isolated and then is reacted with a base C and a Lewis acid.

12. A process as claimed in claim 9 wherein the compound of the formula VIII is prepared in situ without being isolated and then is reacted with a base C and a Lewis acid.

13. A process as claimed in claim 2 further comprising the step of recycling the remaining amount of unreacted compounds of the formulae VII and VIII in the reaction mixture by alkaline hydrolysis with aqueous bases in form of the 2-(2-hydroxy-5-nitrophenyl)-1-aryl-ethanone of formula IV

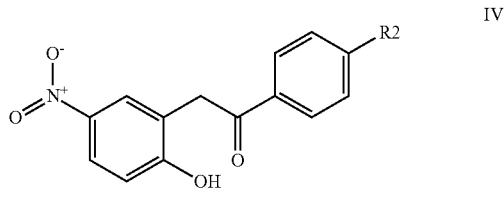

or the corresponding sodium or potassium salt of the formula V

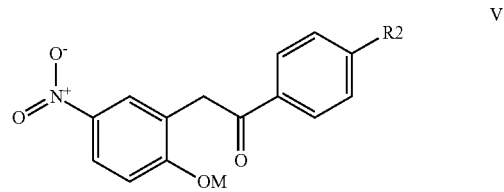

wherein, in the compounds of the formulae IV and V, R2 is methoxy, OCH$_2$C$_6$H$_5$, F, Cl, Br and OCH$_2$CH$_2$CH$_2$N(CH$_2$CH$_2$CH$_2$CH$_3$)$_2$.

14. A process for preparing a compound of the formula VII

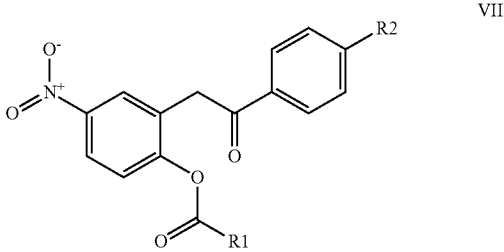

wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, OCH$_2$C$_6$H$_5$, F, Cl, Br or OCH$_2$CH$_2$CH$_2$N(CH$_2$CH$_2$CH$_2$CH$_3$)$_2$;
and salts thereof;

which comprises

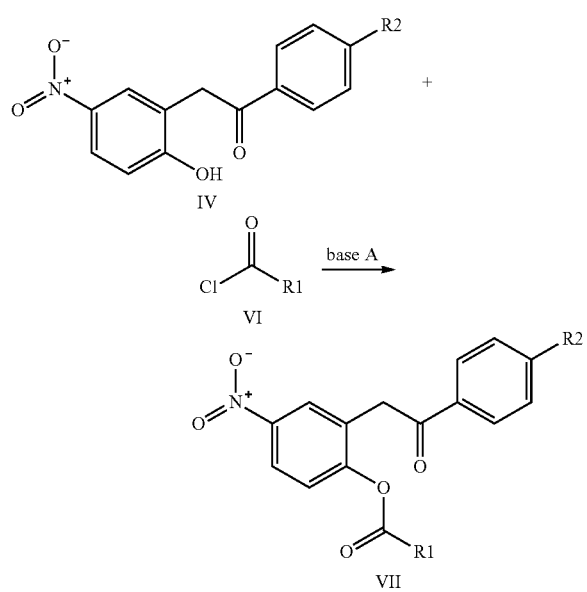

reacting a compound of the formula IV with an acid chloride of the formula VI in the presence of a base A providing the ester of the formula VII;

wherein, in the compound of the formulae IV, R1 and R2 are each as defined in formula VII.

15. A process for preparing a compound of the formula VII

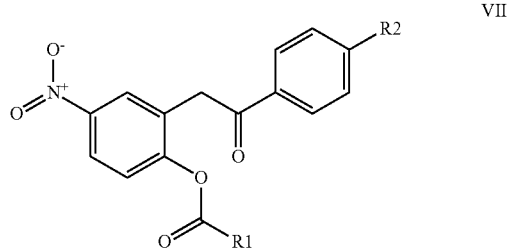

wherein
R1 is alkyl having 1, 2, 3, 4, 5, 6, 7, 8, 9, 10, 11 or 12 carbon atoms or cycloalkyl having 3, 4, 5, 6 or 7 carbon atoms;
R2 is methoxy, $OCH_2C_6H_5$, F, Cl, Br or $OCH_2CH_2CH_2N(CH_2CH_2CH_2CH_3)_2$;
and salts thereof;
which comprises

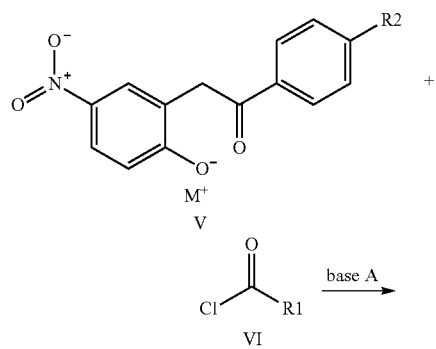

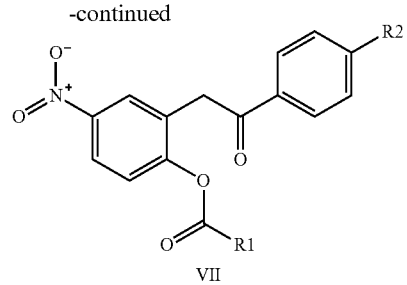

reacting a compound of the formula V with an acid chloride of the formula VI in the presence of a base A providing the ester of the formula VII;

wherein, in the compound of the formulae IV, R1 and R2 are each as defined in formula VII, and M is Na or K.

16. A process as claimed in claim 14 wherein
the base A is selected from the group consisting of triethylamine, diisopropylethylamine, tri-n-butylamine, pyridine, 4-dimethylaminopyridine, NaOH, KOH, $Na_2CO_3$ and $K_2CO_3$.

17. A process as claimed in claim 5 further comprising the step of recycling the remaining amount of unreacted compounds of the formulae VII and VIII in the reaction mixture by alkaline hydrolysis with aqueous bases in form of the 2-(2-hydroxy-5-nitrophenyl)-1-aryl-ethanone of formula IV

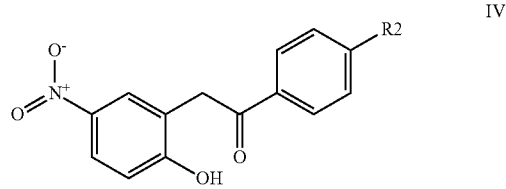

or the corresponding sodium or potassium salt of the formula V

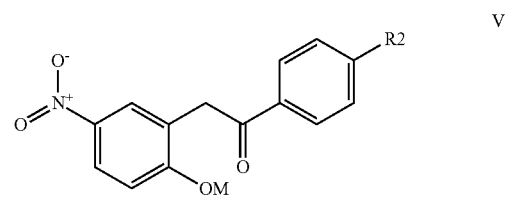

wherein, in the compounds of the formulae IV and V, R2 is methoxy, $OCH_2C_6H_5$, F, Cl, Br or $OCH_2CH_2CH_2N(CH_2CH_2CH_2CH_3)_2$.

18. A process as claimed in claim 9 further comprising the step of recycling the remaining amount of unreacted compounds of the formulae VII and VIII in the reaction mixture by alkaline hydrolysis with aqueous bases in form of the 2-(2-hydroxy-5-nitrophenyl)-1-aryl-ethanone of formula IV

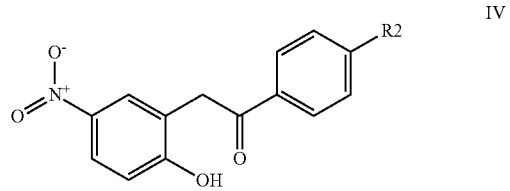

or the corresponding sodium or potassium salt of the formula V

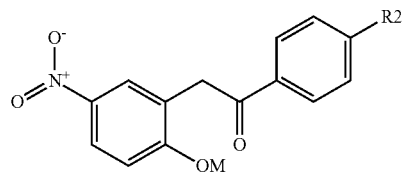

wherein, in the compounds of the formulae IV and V, R2 is methoxy, $OCH_2C_6H_5$, F, Cl, Br or $OCH_2CH_2CH_2N(CH_2CH_2CH_2CH_3)_2$.

19. A process as claimed in claim 15 wherein the base A is selected from the group consisting of triethylamine, diisopropylethylamine, tri-n-butylamine, pyridine, 4-dimethylaminopyridine, NaOH, KOH, $Na_2CO_3$ and $K_2CO_3$.

20. The process as claimed in claim 16 wherein base A is selected from the group consisting of $Na_2CO_3$ and $K_2CO_3$.

21. The process as claimed in claim 19 wherein base A is selected from the group consisting of $Na_2CO_3$ and $K_2CO_3$.

* * * * *